(12) United States Patent
Kulpa et al.

(10) Patent No.: US 11,752,127 B2
(45) Date of Patent: Sep. 12, 2023

(54) METHODS AND COMPOSITIONS FOR TREATMENT OF ANXIETY IN ANIMALS

(71) Applicant: CANOPY GROWTH CORPORATION, Smiths Falls (CA)

(72) Inventors: Justyna Kulpa, Toronto (CA); Dana M. Vaughn, Seguin, TX (US)

(73) Assignee: VIRBAC CORPORATION, Westlake, TX (US)

( * ) Notice: Subject to any disclaimer, the term of this patent is extended or adjusted under 35 U.S.C. 154(b) by 0 days.

(21) Appl. No.: 16/836,142

(22) Filed: Mar. 31, 2020

(65) Prior Publication Data

US 2020/0306219 A1 Oct. 1, 2020

Related U.S. Application Data

(60) Provisional application No. 62/935,795, filed on Nov. 15, 2019, provisional application No. 62/827,734, filed on Apr. 1, 2019.

(51) Int. Cl.
| | | |
|---|---|---|
| *A61K 31/352* | (2006.01) | |
| *A61P 25/22* | (2006.01) | |
| *A61K 9/00* | (2006.01) | |
| *A61K 47/14* | (2017.01) | |

(52) U.S. Cl.
CPC .......... *A61K 31/352* (2013.01); *A61K 9/0053* (2013.01); *A61K 47/14* (2013.01); *A61P 25/22* (2018.01)

(58) Field of Classification Search
CPC ................................................. A61K 31/352
USPC ....................................................... 514/454
See application file for complete search history.

(56) References Cited

FOREIGN PATENT DOCUMENTS

| WO | 2016141056 A1 | 9/2016 |
| WO | 2020102563 A1 | 5/2020 |

OTHER PUBLICATIONS

Moreira, Neural plasticity (2009), 2009, 625469.*
Patel, Neuroscience & Biobehavioral Reviews (2017), 76(Part-A), 56-66.*
Kagan Front Vet Sci. (2019) 5:338.*
Kagan, Kaganm Consumers perceptions of hemp products for animals. J Am Hol Vet Med Assocn. 2016;42:40-48.*
Kogan LR. Dog owners' use and perceptions of cannabis products. J Am Holistic Med Assoc 2018;51:26-33.*
Jurkus, Frontiers in Pharmacology (2016), 7, 454/1-454.*
Morris, Vet. Sci., Sep. 22, 2020, 1-13.*
Yu, Research in Veterinary Science 140 (2021) 38-46.*
Lebkowska-Wieruszewska Beata et al., "Pharmacokinetics of Bedrocan, a cannabis oil extract, in fasting and fed dogs: An explorative study", Research in Veterinary Science, col. 123, Jan. 10, 2019.
Lori Kogan et al., "US Veterinarians' Knowledge, Experience, and Perception Regarding the Use of Cannabidiol for Canine Medical Conditions", Frontiers in Veterinary Science, vol. 5, Jan. 10, 2019.
European Search Report issued in co-pending European application No. 2016750.7 dated Aug. 12, 2020.

\* cited by examiner

*Primary Examiner* — Nizal S Chandrakumar
(74) *Attorney, Agent, or Firm* — BCF LLP

(57) ABSTRACT

The present technology relates to a method for treating anxiety or an anxiety-related disorder in an animal subject, the method comprising administering an effective amount of cannabidiol (CBD) to the animal subject.

11 Claims, 20 Drawing Sheets

METHODS AND COMPOSITIONS FOR TREATMENT OF ANXIETY IN ANIMALS

CROSS-REFERENCE TO RELATED APPLICATIONS

This application claims the benefit of and priority to U.S. provisional patent application No. 62/827,734, filed on Apr. 1, 2019; and of U.S. provisional patent application No. 62/935,795, filed on Nov. 15, 2019, the content of both of which is herein incorporated in entirety by reference.

FIELD

The present technology generally relates to methods for treatment of anxiety and anxiety-related disorders in animals. The present technology also generally relates to compositions for treatment of anxiety or anxiety-related disorders in animals.

BACKGROUND

Anxiety and anxiety-related disorders are broadly defined as excessive fear, worry, obsessions, and/or compulsions. The underlying pathophysiology of anxiety is largely unknown; however functional alterations in the limbic system and dysfunction of the hypothalamic-pituitary-adrenal (HPA) axis have been repeatedly implicated. In particular, regulation of the endocannabinoid system (ECS) and dysregulation of monoamine neurotransmitters (e.g., serotonin) have been examined with regards to regulating fear and mood in the neuronal circuits.

*Cannabis* comprises hundreds of compounds, including phytocannabinoids that can modulate various components of the central nervous system (CNS) including the ECS, and serotonergic activity. In *Cannabis*, over 100 phytocannabinoids have been identified, two of them: 9-Δ-tetrahydrocannabinol (THC) and cannabidiol (CBD) have been thoroughly investigated. THC is considered psychoactive and acts on $CB_1$—and to a lesser extent—$CB_2$ receptors ($CB_1R$, $CB_2R$). THC is a partial agonist to $CB_1Rs$ which are primarily located on presynaptic terminals and supress neurotransmitter release in the CNS. Preclinical data suggests that activation of $CB_1R$ has bimodal and possibly regional-specific control of anxiety, whereby low doses of $CB_1R$ agonist are anxiolytic by acting on cortical glutamatergic neurons, and high doses are anxiogenic, mediated by $CB_1Rs$ on forebrain GABAergic neurons. This observation is consistent in rodents and humans, whereby low doses of THC are generally anxiolytic and high doses are anxiogenic, however, the specific doses in patients with anxiety and related disorders have yet to be identified. Moreover, there is evidence that activation of $CB_1R$ signalling is required for glucocorticoid-mediated feedback inhibition of the HPA axis, which may alleviate symptoms of anxiety.

In contrast to THC, CBD is a non-intoxicating cannabinoid exhibiting low affinity for $CB_1R$ and $CB_2R$. CBD acts on receptors outside of the ECS, including the 5-$HT_{1A}$ receptor (5-$HT_{1A}R$). The 5-$HT_{1A}R$ is an established anxiolytic target, where agonists are currently used in the treatment of generalized anxiety disorder (GAD). In preclinical studies, CBD has been shown to be anxiolytic, primarily by facilitating 5-$HT_{1A}R$ signalling but not by $CB_1Rs$. However, CBD can also activate transient receptor potential cation channel subfamily member 1 (TRPV1) which can be anxiogenic. The clinical efficacy of CBD in animal subjects with anxiety and anxiety-related disorders has not yet been demonstrated.

As such, there remains a need in the field of technology for improved methods and compositions for treatment and/or management of anxiety and anxiety-related disorders in animals.

SUMMARY

Without wishing to be bound to any specific theory, embodiments of the present technology have been developed based on the elucidation by the present discoverers that administration of cannabidiol in dogs decreases elevated serum cortisol levels associated with situational stress and anxiety.

According to various aspects, the present technology thus relates to a method for treating anxiety or an anxiety-related disorder in an animal subject. The method comprises administering an effective amount of cannabidiol to the animal subject. In some instances, the anxiety or anxiety-related disorder is caused by an anxiety-inducing situation (e.g., car ride or noise).

According to various aspects, the present technology relates to a method for facilitating management of anxiety or an anxiety-related disorder in an animal subject. The method comprises administering an effective amount of cannabidiol to the animal subject suffering from anxiety or from an anxiety-related disorder.

According to other various aspects, the present technology relates to a method for reducing an elevated level of cortisol in an animal subject. The method comprises administering an effective amount of cannabidiol to the animal subject having the elevated cortisol level. In some instances, the elevation or increase in cortisol level is caused by anxiety or by an anxiety-related disorder which may be triggered by an anxiety-inducing situation (e.g., car ride or noise).

Other aspects and features of the present disclosure will become apparent to those ordinarily skilled in the art upon review of the following description of specific embodiments in conjunction with the accompanying drawings.

BRIEF DESCRIPTION OF THE DRAWINGS

All features of embodiments which are described in this disclosure are not mutually exclusive and can be combined with one another. For example, elements of one embodiment can be utilized in the other embodiments without further mention. A detailed description of specific embodiments is provided herein below with reference to the accompanying drawings in which.

DETAILED DISCLOSURE

Figure 1:
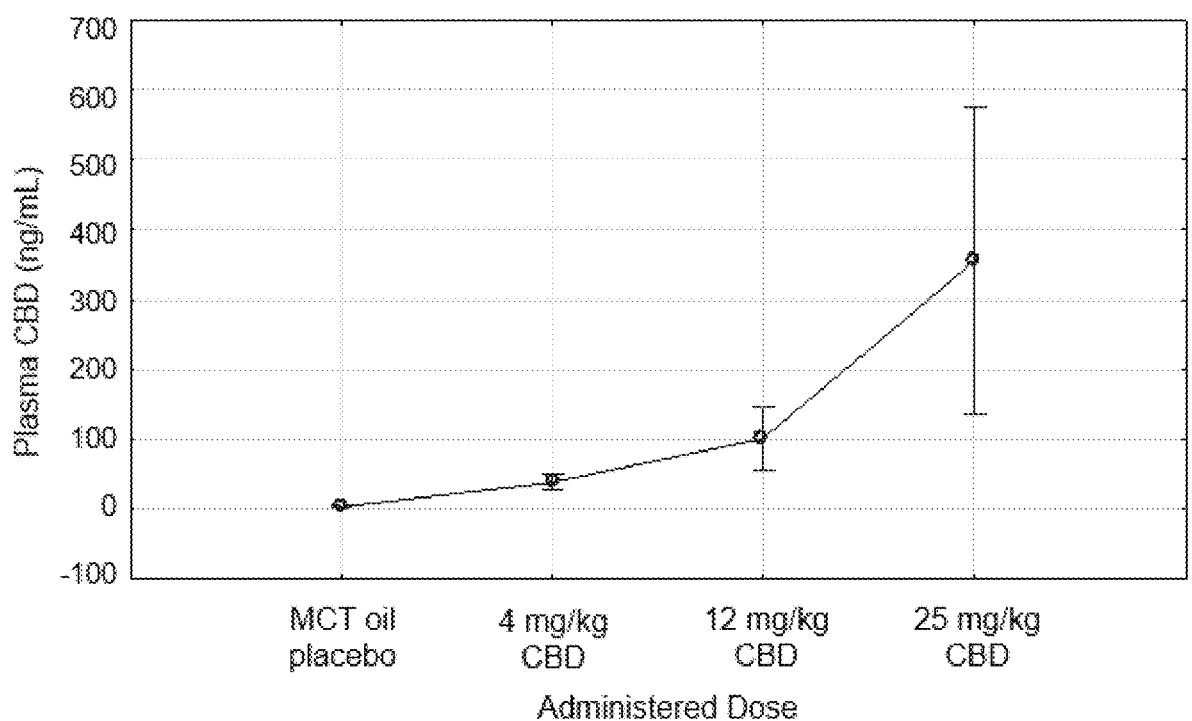
FIG. 1 is a graph showing serum CBD levels in the tested dogs as a function of dose from samples taken post-car ride; current effect $F(2, 42)=10.111$; $p=0.00004$.

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which variations and additions do not depart from the present technology. Hence, the following description is intended to illustrate some particular embodiments of the technology, and not to exhaustively specify all permutations, combinations and variations thereof.

As used herein, the singular form "a," "an" and "the" include plural referents unless the context clearly dictates otherwise.

The recitation herein of numerical ranges by endpoints is intended to include all numbers subsumed within that range (e.g., a recitation of 1 to 5 includes 1, 1.25, 1.5, 1.75, 2, 2.45, 2.75, 3, 3.80, 4, 4.32, and 5).

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "comprise" is used in its non-limiting sense to mean that items following the word are included, but items not specifically mentioned are not excluded.

As used herein, the term "*Cannabis*" refers to the genus of flowering plants in the family Cannabaceae. Three species, subspecies or varieties may be recognized as being part of the *Cannabis* genus, namely: *Cannabis sativa, Cannabis indica*, and *Cannabis ruderalis*. The expressions "*Cannabis sativa*" and "*C. sativa*" are used herein interchangeably. The term "variety" as used herein refers to different chemovars or cultivars of the plant genus *Cannabis*. For example, the term "variety" can refer to different pure or hybridized *cannabis* plants. In some instances, the *cannabis* variety of the present technology can be a hybrid of two varieties, for example, a hybrid between *C. sativa* and *C. indica*. Different *cannabis* varieties often exhibit distinct chemical compositions with characteristic levels of cannabinoids and terpenes, as well as other components.

As used herein, the term "cannabinoid" refers to a chemical compound belonging to a class of secondary compounds commonly found in plants of genus *cannabis*, but also encompasses synthetic and semi-synthetic cannabinoids. The most notable cannabinoid is tetrahydrocannabinol (THC), the primary psychoactive compound in *cannabis*. Cannabidiol (CBD) is another cannabinoid that is a major constituent of the phytocannabinoids. There are at least 113 different cannabinoids isolated from *cannabis*, exhibiting varied effects. Synthetic cannabinoids and semi-synthetic cannabinoids encompass a variety of distinct chemical classes, for example and without limitation: the classical cannabinoids structurally related to THC, the non-classical cannabinoids (cannabimimetics) including the aminoalkylindoles, 1,5 diarylpyrazoles, quinolines, and arylsulfonamides as well as eicosanoids related to endocannabinoids. In many cases, a cannabinoid can be identified because its chemical name will include the text string "*cannabi*". However, there are a number of cannabinoids that do not use this nomenclature. Within the context of this disclosure, where reference is made to a particular cannabinoid, each of the acid and/or decarboxylated forms are contemplated as both single molecules and mixtures. In addition, salts of cannabinoids are also encompassed, such as salts of cannabinoid carboxylic acids. As well, any and all isomeric, enantiomeric, or optically active derivatives are also encompassed. In particular, where appropriate, reference to a particular cannabinoid includes both the "A Form" and the "B Form". For example, it is known that THCA has two isomers, THCA-A in which the carboxylic acid group is in the 1 position between the hydroxyl group and the carbon chain (A Form) and THCA-B in which the carboxylic acid group is in the 3 position following the carbon chain (B Form).

As used herein, the term "purified" means extracted, isolated, and/or separated from other compounds, formulations, compositions, matter, and/or mass resulting in a greater than 60% purity. In some embodiments a "purified" cannabinoid (or "purified" terpene) is greater than about 70% pure, greater than 75% pure, greater than about 80% pure, greater than 85% pure, greater than about 90% pure, greater than about 91% pure, greater than about 92% pure, greater than about 93% pure, greater than about 94% pure, greater than about 95% pure, greater than about 96% pure, greater than about 97% pure, greater than about 98% pure, or greater than about 99% pure. Within the context of the present disclosure, where a compound comprises stereogenic centers, the term "purified" includes enantiomerically pure compositions and also mixtures of enantiomers or isomers. Also within the context of the present disclosure, purified compounds may be purposely formulated with other compounds at various levels of purity. Provided that the ingredients used for purposeful formulation are purified prior to the said purposeful formulation, the act of subsequently formulating them does render them not "purified" within the context of an ingredient list. In an embodiment, the term "purified" may refer to a cannabinoid that is separated from plant matter from which it was derived. In an embodiment, the term "purified" may refer to a terpene that is separated from plant matter from which it was derived.

As used herein, the term "animal" refers to any non-human animal, including mammals, birds, reptiles, marsupials, amphibians, and fish. In some instances, the term "animal" refers to domesticated animals, such as: a cow, horse, sheep, pig, goat, chicken, turkey, quail, duck, goose, cat, dog, mouse, rat, rabbit, or guinea pig. In some further instances, the term "animal" refers to dogs, cats, or horses. The term "animal" also includes wild, non-domesticated animals and exotic animals in captivity, for instance, undomesticated "pets" and animals held in zoological or other captive environments.

In one embodiment, the present technology relates to a method for treating anxiety or an anxiety-related disorder in an animal. The method comprises administering an effective amount of cannabidiol (CBD) to the animal.

In one embodiment, the present technology relates to a method for treating anxiety or an anxiety-related disorder in a dog. The method comprises administering an effective amount of cannabidiol (CBD) to the dog.

As used herein, the term "treatment" refers to administering a substance (e.g., cannabidiol) effective to ameliorate symptoms associated with a disease (e.g., anxiety or anxiety-related disorder), to lessen the severity or cure the disease, to prevent the disease from occurring or to facilitate the management of the disease or disorder or the symptoms associated with the disease or disorder. As used herein, the term "manage" or "management" refers to the process of dealing with or controlling the disease or the disorder (e.g., anxiety or anxiety-related disorder). The subjects in need of treatment are also those in which the disorder, disease, condition or medical condition has occurred and left aftereffects. Treatment also refers to administering a substance effective to improve or ameliorate symptoms associated with a disease, a disorder, condition or medical condition to lessen the severity of or cure the disease, disorder, condition or medical condition, or to prevent the disease, disorder or condition from occurring.

Anxiety refers to a feeling of worry, nervousness, or unease, typically about an imminent event or something with an uncertain outcome. Anxiety-related disorders are a group of mental disorders characterized by feelings of anxiety and/or fear. These feelings may cause physical symptoms, such as a fast heart rate and shakiness. Fear is the instinctual feeling of apprehension resulting from a situation, person, or object presenting an external threat, whether real or perceived. The response of the autonomic nervous system prepares the body for the freeze, fight, or flight syndrome. It is considered to be a normal behavior, essential for adaptation and survival; its context determines whether the fear response is normal, or abnormal and inappropriate. Most abnormal reactions are learned and can be unlearned with gradual exposure. Moreover, the persistent and excessive fear of a specific stimulus is referred to as a phobia; it is a persistent and excessive fear of a specific stimulus. It has been suggested that once a phobic event has been experienced, any event associated with it, or the memory of it, is sufficient enough to generate a response. The most common phobias are associated with noises, in particular loud noises (such as thunderstorms or fireworks). Anxiety, meanwhile, is the anticipation of future dangers from unknown or imagined origins that result in normal body reactions (known as physiologic reactions) associated with fear; most common visible behaviors are elimination (i.e., urination and/or passage of bowel movements), destruction, and excessive vocalization (i.e., barking, crying). Separation anxiety is the most common specific anxiety in companion dogs. When alone, the animal exhibits anxiety or excessive distress behaviors. Profound fear and withdrawal of unknown cause (so called idiopathic fear and withdrawal) has also been noted in certain dog breeds, including the Siberian husky, German Shorthaired Pointer, Greyhound, Chesapeake Bay Retriever, Bernese Mountain Dog, Great Pyrenees, Border Collie, and Standard Poodle, among others. There appears to be a strong familial component, with the likelihood of a genetic influence.

Most fears, phobias, and anxieties develop at the onset of sexual maturity, from 12 to 36 months of age. A profound form of fear and withdrawal of unknown cause occurs at 8 to 10 months of age. Old-age-onset separation anxiety of unknown cause may be a variant of a decline in thinking, learning, and memory in elderly dogs.

Examples of symptoms and types of anxiety in dogs include, but are not limited to: mild fears: signs may include trembling, tail tucked, withdrawal, hiding, reduced activity, and passive escape behaviors; panic: signs may include active escape behavior, and increased, out-of-context, potentially injurious motor activity; classic signs of sympathetic autonomic nervous system activity, including diarrhea; Anxieties: lesions secondary to anxious behavior (such as licking and biting at the self).

Examples of causes of fears and anxiety in dogs include, but are not limited to: any illness or painful physical condition increases anxiety and contributes to the development of fears, phobias, and anxieties; aging changes associated with nervous system changes; infectious disease (primarily viral infections in the central nervous system), and toxic conditions, such as lead poisoning, may lead to behavioral problems, including fears, phobias, and anxieties; rear from a terrible experience; dog may have been forced into an unfamiliar and frightening experience; dogs that are deprived of social and environmental exposure until 14 weeks of age may become habitually fearful; phobias and panic may have a history of inability to escape or get away from the stimulus causing the phobia and panic, such as being locked in crate; separation anxiety: history of abandonment, multiple owners, rehoming, or prior neglect is common; exacerbating the condition may be that the dog has been often abandoned or rehomed because of separation anxiety.

In some embodiments of the present technology, cannabidiol may be used to treat, alleviate, or prevent anxiety in a subject in need thereof. Cannabidiol may thus be considered useful for the treatment, prevention or alleviation of anxiety disorders, such as panic disorder with or without agoraphobia, animal and other phobias including social phobias, obsessive-compulsive disorder, and generalized or substance-induced anxiety disorder; stress disorders including post-traumatic and acute stress disorder; sleep disorders; neuroses; convulsive disorders, for example epilepsy, seizures, convulsions, eating disorders; neuralgia, e.g. trigeminal neuralgia; muscle spasm or spasticity, e.g. in paraplegic patients;

As used herein, the expression "effective amount" (also referred to herein as "dosage") of cannabidiol refers to an amount of cannabidiol that is suitable to treat anxiety or an anxiety-related disorder in an animal subject; and/or to an amount of cannabidiol that is suitable to facilitate the management of anxiety or an anxiety-related disorder in an animal subject; and/or an amount of cannabidiol that is suitable to decrease elevated cortisol levels in an animal subject.

In some embodiments, the animal subject afflicted with anxiety or an anxiety-related disorder is an animal. In some instances, the animal is a dog, a cat, a horse, or the like.

In some embodiments, the cannabidiol to be administered to the animal subject is extracted or isolated from the Cannabis plant, in particular from Cannabis sativa according to methods known in the art. Extraction in natural products chemistry is a separation process consisting in the separation of a substance from a matrix of natural materials. It includes liquid-liquid extraction and solid phase extraction. The distribution of any given compound or composition (hereinafter desired material) between two phases is an equilibrium condition described by partition theory. This is based on exactly how the desired material moves from the water into an organic layer. Suitably, the desired material is substantially free of impurities other than solvent of other extraction reagents, more suitably it is about 10%, 20%, 30%, 40%, 50%, 60%, 70%, 80%, or 85% free of said impurities, more suitably it is about 90% free of said impurities, more suitably yet, the desired material is about 95% free of impurities other than solvents or other extraction reagents.

In some instances, the cannabidiol is a *cannabis* extract enriched in cannabidiol with low delta-9-tetrahydrocannabinol content.

Extractions often use two immiscible phases to separate a solute such as the desired material from one phase into the other. Typical laboratory extractions are of organic compounds such as the desired material out of an aqueous phase and into an organic phase. Suitable extractant systems arranged in order of their typical preferability include, by way of example and not limitation, ethyl acetate<acetone<ethanol<methanol<acetone: water (7:3) <ethanol: water (8:2)<methanol: water (8:2)<water, etc., in increasing order of polarity according to the Hildebrand solubility parameter. The extract can be put back to dried or other form using, by way of example and not limitation, a centrifugal evaporator or a freeze-drier. Extraction of compositions or components of the present technology may be prepared by butane extraction of *Cannabis*. Modern more technical techniques include supercritical carbon dioxide extraction, ultrasonic extraction, heat reflux extraction, mechanochemical-assisted extraction, microwave-assisted extraction, instant controlled pressure drop extraction (DIC), and perstraction. Perstraction is the separation technique developed from liquid-liquid extraction. Due to the presence of the membrane a wider selection of extractants can be used, this can include the use of miscible solutions, for example the recovery of ammonia from waste water using sulphuric acid. This process is analogous to pervaporation in some way but the permeate is in liquid phase. Perstraction technique eliminates the problem of phase dispersion and separation altogether. A basic perstraction is called the single perstraction or membrane perstraction. An advantage is minimizing toxic damage to microorganisms or enzymes. Perstraction has been combined with the ABE (acetone butanol ethanol) fermentation for butanol production. Butanol is toxic to the fermentation; therefore perstraction can be applied to remove the butanol from the vicinity of the bacteria as soon as it is produced. Liquid-liquid extraction (LLE) was combined with the ABE fermentation for in situ product recovery, but the extractants with the highest affinity for butanol tend to be toxic to the bacteria. The application of LLE would also require the extractant to be sterilized prior to contact with the fermentation broth. Perstraction can overcome these problems due to a membrane separating the fermentation broth from the extractant.

Fractionation is a separation process in which a certain quantity of any given compound or composition (hereinafter desired material), by way of example and not limitation, a desired material, solid, liquid, enzymes, suspension, or isotope, is divided during a phase transition, into many smaller quantities (fractions) in which the desired material varies according to a gradient. Fractions are collected based on differences in a specific property of the individual components. A common trait in fractionations is the need to find an optimum between the number of fractions collected and the desired purity in each fraction. Fractionation makes it possible to isolate more than two components in a mixture in a single run. This property sets it apart from other separation techniques.

Filtration is a mechanical method to separate solids from liquids or gases by passing the feed stream through a porous sheet such as a cloth or membrane, which retains the solids and allows the liquid to pass through. Centrifugation is a process in which light particles are revolved at high speed with the help of an electric motor so that the fine particles which do not settle at bottom would settle down. Evaporation is used to remove volatile liquids from non-volatile solutes which cannot be done through filtration due to the small size of the substances. Liquid-liquid extraction removes an impurity or recovers a desired product by dissolving the crude material in a solvent in which other components of the feed material are soluble. Crystallization separates a product from a liquid feed stream, often in extremely pure form, by cooling the feed stream or adding precipitants which lower the solubility of the desired product so that it forms crystals. The pure solid crystals are then separated from the remaining liquor by filtration or centrifugation. Recrystallization: In analytical and synthetic chemistry work, purchased reagents of doubtful purity may be recrystallized, e.g. dissolved in a very pure solvent, and then crystallized, and the crystals recovered, to improve and/or verify their purity. Adsorption removes a soluble impurity from a feed stream by trapping it on the surface of a solid material such as activated carbon which forms strong non-covalent chemical bonds with the impurity. Chromatography employs adsorption and desorption on a packed bed of a solid to purify multiple components of a single feed stream. Many common methods of purification include, by way of example and not limitation; distillation, widely used in petroleum refining and in purification of ethanol separates volatile liquids based on their relative volatilities; water purification combines many methods to produce potable or drinking water; downstream processing refers to purification of chemicals, pharmaceuticals and food ingredients produced by fermentation or synthesized by plant and animal tissues, for example antibiotics, citric acid, vitamin E, and insulin; electrolysis refers to the breakdown of substances using an electric current. This removes impurities in a substance that an electric current is run through; sublimation is the process of changing of any substance (usually on heating) from a solid to a gas (or from gas to a solid) without passing through liquid phase; and bioleaching is the extraction of desired materials from their matrix of biological material using living organisms.

There are also many other methods for obtaining fractions of desired material such as, by way of example and not limitation; adsorption, adhesion of atoms, ions or molecules of gas, liquid, or dissolved solids to a surface; capillary electrophoresis; centrifugation and cyclonic separation, separates based on density differences; chromatography separates dissolved substances by different interaction with (i.e., travel through) a material; crystallization; decantation; demister (vapor), removes liquid droplets from gas streams; distillation, used for mixtures of liquids with different boiling points; drying, removes liquid from a solid by vaporization; electrophoresis, separates organic molecules based on their different interaction with a gel under an electric potential (i.e., different travel); electrostatic separation, works on the principle of corona discharge, where two plates are placed close together and high voltage is applied. This high voltage is used to separate the ionized particles; elutriation; evaporation; leaching; field flow fractionation; flotation; dissolved air flotation, removes suspended solids nonselectively from slurry by bubbles that are generated by air coming out of solution; froth flotation, recovers valuable, hydrophobic solids by attachment to air bubbles generated by mechanical agitation of an air-slurry mixture, which float, and are recovered; flocculation, separates a solid from a liquid in a colloid, by use of a flocculant, which promotes the solid clumping into flocs; filtration—Mesh, bag and paper filters are used to remove large particulates suspended in fluids (e.g., fly ash) while membrane processes including microfiltration, ultrafiltration, nanofiltration, reverse osmosis, dialysis (biochemistry) utilizing synthetic membranes, separates micrometer-sized or smaller species; fractional freezing; oil-water separation, gravimetrically separates suspended oil droplets from waste water in for example oil refineries, petrochemical and chemical plants, natural gas processing plants and similar industries; magnetic separation; precipitation; recrystallization; scrubbing, separation of particulates (solids) or gases from a gas stream using liquid; sedimentation, separates using vocal density pressure differences; gravity separation; sieving; stripping; sublimation; vapor-liquid separation, separates by gravity, based on the Souders-Brown equation; winnowing; zone refining. One of ordinary skill in the art of natural products extraction and isolation could devise many more methods of fractionating said desired materials.

In some other implementations of these embodiments, the cannabidiol to be used in the methods and compositions of the present technology may be synthesized de novo.

An effective amount of cannabidiol according to the various embodiments of the present technology will vary between animal subject to be treated and will depend, among other things, upon the effect or result to be achieved, the condition of the subject and the route of delivery. In some embodiments, an effective amount is from about 0.1 mg/kg to about 100 mg/kg, or from about 1 mg/kg to about 100 mg/kg. In some other embodiments, an effective amount is from about 0.1 mg/kg to about 50 mg/kg, or from about 1 mg/kg to about 50 mg/kg. In some instances, the effective amount is from about 0.1 mg/kg to about 25 mg/kg, or from about 1 mg/kg to about 25 mg/kg.

In some other instances, the effective amount is about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, about 50 mg/kg, about 75 mg/kg, or about 100 mg/kg or more may be used.

In some embodiments, the present technology relates to a composition comprising cannabidiol to be used in the methods of the present technology. In some implementations of these embodiments, the composition comprises an amount of cannabidiol effective to treat anxiety or an anxiety-related disorder in an animal.

In some instances, the cannabidiol is mixed with other components to form a composition comprising the cannabidiol. For example, the cannabidiol may be mixed (e.g., diluted) with a cannabidiol suitable diluent. Examples of cannabidiol suitable diluent include but are not limited to, non-polar chemical substances such as oil. An example of non-polar chemical substance into which the cannabidiol may be diluted with is a medium-chain triglyceride (MCT)-containing oil (e.g., sunflower oil, coconut oil, kernel oil or the like). A person skilled in the art will appreciate the cannabidiol suitable diluents that may be used to prepare the compositions of the present technology.

In some other embodiments, the compositions of the present technology may comprise a carrier oil. The carrier oil is, optionally, food grade, does not adversely affect product quality (such as appearance, taste, texture, or stability), protects from chemical degradation during storage and distribution, and/or increases bioavailability following ingestion by, for example, aiding dissolution or absorption. Carrier oils can help stabilize emulsions and can have an effect on the physicochemical stability of emulsions in the gastrointestinal tract (GI Tract). The rate and extent of lipid digestion is generally higher for MCT emulsions than for LCT emulsions, which is attributed to differences in the water dispersibility of the medium and long chain fatty acids formed during lipolysis. The total bioavailability of active components after digestion can be higher for LCT emulsions than for MCT emulsions but both may be used. In embodiments of the compositions of the present technology, the carrier oil may be synthesized or isolated from a natural source. In some embodiments, the carrier oil is a natural oil as known in the art, such as an edible vegetable oil. In some alternative embodiments, the carrier oil is a synthetic edible oil, such as a hydrogenated vegetable oil, a medium-chain triglyceride (MCT) oil, and the like. For example, the carrier oil may be selected from one or more of the following classes, without limitation: medium-chain triglycerides (MCT) oil, medium-chain fatty acids (e.g., caproic acid, caprylic acid, capric acid, lauric acid, long-chain triglycerides (LCT oil), long chain fatty acids (e.g., myristic acid, palmitic acid, stearic acid, arachidic acid, linoleic acid), glycerine/glycerol, Maisine®CC, glycerol monolinoleate, coconut oil, corn oil, canola oil, olive oil, avocado oil, vegetable oil, flaxseed oil, palm oil, palm kernel oil, peanut oil, sunflower oil, rice bran oil, safflower oil, jojoba oil, argan oil, grapeseed oil, castor oil, wheat germ oil, *arnica* oil, peppermint oil, hemp oil, sesame oil, pomegranate seed oil, terpenes, terpenoids, beta-myrcene, linalool, α-pinene, beta-pinene, beta-caryophyllene, caryophyllene oxide, α-humulene, nerolidol, D-limonene, L-limonene, para-cymene, eugenol, farnesol, geraniol, phytol, menthol, terpineol, α-terpineol, benzaldehyde, hexyl acetate, methyl salicylate, eucalyptol, ocimene, terpinolene, α-terpinene, isopulegol, guaiol, α-bisabolol and combinations thereof. Other suitable carrier oils include Labrasol, LabrafacLipophile WL 1349, Labrail M1944, Peceol, Plurol Oliqiue CC 497, Transcutol HP, Tween 80, Gelucire 48/16, and combinations thereof. Carrier oils may also be in the form of an oil powder, such as a plant or animal-derived oil powder (such as rice bran oil powder, coconut oil powder, grape seed oil powder, cranberry seed oil powder, chia seed oil powder, flaxseed oil powder, MCT oil powder, hydrolyzed collagen powder, saw palmetto oil powder, safflower oil powder, evening primrose seed oil powder, fish oil powder, or the like.). In some embodiments, the carrier oil is medium-chain triglycerides (MCT), e.g., MCT oil or MCT oil powder. In other embodiments, the carrier oil is Maisine®CC.

In some embodiments, the cannabidiol is in a form suitable for oral administration, rectal administration, enteric administration, sublingual administration, intradermal administration, intravenous administration or transdermal administration, although the most suitable route in any given case will depend on the nature and severity of the anxiety and the anxiety-related disorder to be treated. In some instances, the cannabidiol is in a form suitable for oral administration.

In the embodiments wherein the composition is suitable for oral administration, the composition may comprise any additional elements that may be appealing or pleasing to the animal to be treated to facilitate oral intake.

In some embodiments, the compositions of the present technology may be in the form of a pharmaceutical composition. The pharmaceutical composition may include the cannabidiol as well as a pharmaceutically acceptable excipient.

In addition to the cannabidiol, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol.

A composition in accordance with the present technology comprising cannabidiol, may be prepared by conventional procedures for blending and mixing compounds. Preferably, the composition also includes an excipient, most preferably a pharmaceutical excipient. Compositions containing an excipient and incorporating the cannabidiol may be prepared by procedures known in the art. For example, cannabidiol may be formulated into tablets, capsules, powders, suspensions, solutions for oral administration and solutions for parenteral administration including intravenous, intradermal, intramuscular, and subcutaneous administration, and into solutions for application onto patches for transdermal application with common and conventional carriers, binders, diluents, and excipients.

In some embodiments, pharmaceutical compositions of the present technology comprise cannabidiol together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. Pharmaceutical compositions of the present technology may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intra-arterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

Cannabidiol, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Similarly, cachets and lozenges are included. Tablets, powders, capsules, pills, cachets, and lozenges can be used as solid forms suitable for oral administration. Liquid preparations include solutions, suspensions, and emulsions, for example, water or waterpropylene glycol solutions. For example, parenteral injection liquid preparations can be formulated as solutions in aqueous polyethylene glycol solution. Cannabidiol may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents.

For topical administration to the epidermis, cannabidiol may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or coloring agents.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of cannabidiol. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In some embodiments, the compositions of the present technology may be formulated into extended release dosage form. As used herein, the term "extended release" is characterized by the gradual release of cannabidiol from the composition over an extended period of time, optionally greater than about 30 minutes. With extended release, the rate of release of cannabidiol from the composition is controlled in order to maintain therapeutic activity of cannabidiol for a longer period of time. In certain embodiments, the composition may release cannabidiol over a period of about 12 hours to about 24 hours.

In some embodiments, the compositions of the present technology may be formulated in to a kit. In such embodiments, the composition may be placed in an appropriate container and labeled for treatment of anxiety or an anxiety-related disorder. For administration of the composition, such labeling may include instructions concerning the amount, frequency and method of administration, thus forming a kit for administration of the compositions of the present disclosure.

EXAMPLES

The examples below are given so as to illustrate the practice of various embodiments of the present disclosure. They are not intended to limit or define the entire scope of this disclosure. It should be appreciated that the disclosure is not limited to the particular embodiments described and illustrated herein but includes all modifications and variations falling within the scope of the disclosure as defined in the appended embodiments.

Example 1—Study Design: Car Ride Model

A Car-Ride Model for fear and anxiety was used to assess the anxiolytic properties of a cannabidiol formulation on dog subjects. One of the objectives of this study was to determine the anxiolytic effectiveness of orally dosed CBD-enriched cannabidiol formulation at three dose levels, namely at: 4 mg/kg CBD; 12 mg/kg CBD; and 25 mg/kg CBD as compared to a placebo control in a car ride model of fear and anxiety.

Enrollment into the study was based on the subject's baseline activity response to a car ride. Twenty-four (24) Beagle Dogs were screened for car-ride induced elevation of blood cortisol. The initial screening occurred over a 10-day period. Sixteen of the 24 dogs were selected to be used in the subsequent efficacy trial. The schedule of operations for the baseline screen is outlined in Table 1.

TABLE 1

Schedule of operations for Baseline Screen

| Test day | Procedure | Comments |
|---|---|---|
| −8 | Veterinary exam, blood chemistry | Body weight |
| −7 | Baseline cortisol | Cohort 1 |
| −6 | Baseline cortisol/Car ride | Cohort 2/Cohort 1 |
| −5 | Car ride | Cohort 2 |
| −4 to −1 | Data analysis | Subject Selection |
| 0 | Group assessment | Body weight |

The subsequent dose-finding efficacy trial was a blinded pre-clinical trial with sixteen (16) dogs. Dogs were allocated to four treatment groups each containing four (4) dogs based on the baseline response to the car-ride model. In the car-ride model, the dogs were placed in a travel crate secured in the back of a transport vehicle. Anxiety was assessed by monitoring behavior and heart rate during the car ride, and by blood cortisol measures after the car ride. A Williams design was used in which 3 dose levels of the drug and a placebo control were evaluated, with every dog being tested on every condition. Thus, the study had four cycles: four (4) groups of four (4) dogs each, with two (2) males and two (2) females per group, were given four (4) cycles of either one of three increasing doses of a cannabidiol-enriched liquid formulation or the vehicle (medium chain triglyceride solution without cannabidiol), each in a volume of 4 mL. Actives or placebo were administered on the fourth day of each cycle, four (4) hours (±15 minutes) before exposure to a 10-minute car ride in a controlled setting. Each dosing cycle was seven (7) days, so there were seven (7) days between doses.

Anxiety behavioral data measures were recorded, as was serum cortisol levels (an anxiety/stress-related biomarker), heart rate and blood cannabidiol content. Subjects were dosed once during each arm, approximately four (4) hours prior to the car ride test. Blood samples for measurements of cortisol and CBD were taken on two occasions during each arm. The first was on day 1, a no treatment day. The second was within 10 minutes (±2 minutes) following the car ride. Both blood samples were taken as closely as possible to the same time of day. Heart rate was continuously measured during the car ride. There were seven days of washout between treatment days. For the sake of scheduling, the 16 dogs were tested in two cohorts, with eight (8) dogs tested per cohort day. The test schedule that followed is outlined in Table 2.

TABLE 2

Schedule of Operations for the Treatment Phase

| Study Day | Procedures |
|---|---|
| 1 | Cohort 1: Baseline blood cortisol and cannabidiols - taken at time point that corresponds to time point when cortisol will be taken after the car ride. |
| 2 | Cohort 1: Test Article Administration Car Ride & Heart Rate Monitoring. Post Ride Blood Collection for analysis of cortisol and cannabidiols.<br>Cohort 2: Baseline blood cortisol and cannabidiols - taken at time point that corresponds to time point when cortisol will be taken after the car ride. |
| 3 | Cohort 2: Test Article Administration Car Ride & Heart Rate Monitoring Post Ride Blood Collection for analysis of cortisol and cannabidiols. |
| 8 | Cohort 1: Baseline blood cortisol and cannabidiols - taken at time point that corresponds to time point when cortisol will be taken after the car ride. Body Weights. |
| 9 | Cohort 1: Test Article Administration Car Ride & Heart Rate Monitoring. Post Ride Blood Collection for analysis of cortisol and cannabidiols.<br>Cohort 2: Baseline blood cortisol and cannabidiols - taken at time point that corresponds to time point when cortisol will be taken after the car ride. |
| 10 | Cohort 2: Test Article Administration Car Ride & Heart Rate Monitoring Post Ride Blood Collection for analysis of cortisol and cannabidiols. |
| 15 | Cohort 1: Baseline blood cortisol and cannabidiols - taken at time point that corresponds to time point when cortisol will be taken after the car ride. Body Weights. |
| 16 | Cohort 1: Test Article Administration Car Ride & Heart Rate Monitoring. Post Ride Blood Collection for analysis of cortisol and cannabidiols.<br>Cohort 2: Baseline blood cortisol and cannabidiols - taken at time point that corresponds to time point when cortisol will be taken after the car ride. |
| 17 | Cohort 2: Test Article Administration Car Ride & Heart Rate Monitoring Post Ride Blood Collection for analysis of cortisol and cannabidiols. |
| 22 | Cohort 1: Baseline blood cortisol and cannabidiols - taken at time point that corresponds to time point when cortisol will be taken after the car ride. Body Weights. |
| 23 | Cohort 1: Test Article Administration Car Ride & Heart Rate Monitoring. Post Ride Blood Collection for analysis of cortisol and cannabidiols.<br>Cohort 2: Baseline blood cortisol and cannabidiols - taken at time point that corresponds to time point when cortisol will be taken after the car ride. |
| 24 | Cohort 2: Test Article Administration Car Ride & Heart Rate Monitoring Post Ride Blood Collection for analysis of cortisol and cannabidiols. |

Treatment conditions as follows: High Dose: 25 mg/kg CBD; Medium Dose: 12 mg/kg CBD; Low Dose: 4 mg/kg CBD; Placebo control: MCT (Medium Chain Triglyceride) solution. The animals were handled and cared for as similarly as possible throughout the study. The study used a Williams design. The experimental unit were one individual dog and the number of dogs per treatment sequence was four (4), each containing two (2) males and two (2) females. The treatment sequence is summarized in Table 3.

TABLE 3

Treatment Sequences

| | Treatment | | | |
|---|---|---|---|---|
| Sequence | Cycle 1<br>Days 1, 2, 3 | Cycle 2<br>Days 8, 9, 10 | Cycle 3<br>Days 15, 16, 17 | Cycle 4<br>Days 22, 23, 24 |
| A | High-Dose | Medium-Dose | Placebo | Low-Dose |
| B | Medium-Dose | Low-Dose | High-Dose | Placebo |
| C | Low-Dose | Placebo | Medium-Dose | High-Dose |
| D | Placebo | High-Dose | Low-Dose | Medium-Dose |

Within sex, dogs were ranked in descending order (e.g. the animal with the greatest elevation of cortisol from baseline will receive a rank of 1, and the animal with the lowest elevation of cortisol will receive a rank of 8). In the event that two or more animals had the same score, animals with the same score were ranked alphanumerically (A-Z) by animal identification name. These rankings were used for blocking. Animals were first stratified by sex, and then within sex be blocked by response score. Block 1 for each sex consisted of the four lowest ranking dogs, block 2 for each sex consisted of the four highest ranking dogs. Dogs were then allocated into four groups using a randomized block procedure, with one animal per block assigned to each test group. Allocation of Groups to a Treatment Group: Allocation of Groups was done randomly. First, the words "Sequence A", "Sequence B", "Sequence C" and "Sequence D" were each written on one of the four identical pieces of paper. Next, the papers were placed into an opaque container. The designated non-blinded personnel removed one piece of paper and assigned Group 1 to that treatment sequence. The second drawn paper was used to assign Group 2 to the sequence written on the paper. The third drawn paper was used to assign Group 3 to the treatment sequence written on the paper. The fourth drawn paper was used to assign Group 4 to the treatment sequence written on the paper. Each group followed one of the four treatment sequences as depicted in Table 2.

The study was a blinded pre-clinical trial carried out in a standardized environment. Sixteen (16) dogs (8 males and 8 females) were included in the study. A Williams design, in which all test subjects receive all three dosages and one placebo were used. Four (4) groups of four (4) dogs each, with two (2) males and two (2) females per group, will be given four (4) cycles of either one of three increasing doses of a Cannabidiol-enriched liquid formulation or the vehicle (medium chain triglyceride solution without cannabidiol), each in a volume of 4 mL. Actives or placebo were administered on the fourth day of each cycle, four (4) hours (±15 minutes) before exposure to a 10-minute car ride. Each dosing cycle is seven (7) days, so there were seven (7) days between doses. Anxiety behavioral data measures were recorded, as was cortisol (an anxiety/stress-related biomarker), and heart rate. Cortisol measures were taken within 5 minutes of car ride completion. The Schedule of Operations can be found in Table 2.

Dogs participated in the car ride procedure individually (one dog per 10 minute car ride). Each dog was removed from its home pen approximately 10 minutes prior to their test session. A Polar H7 monitor was attached and 3 minutes baseline heart rate collected after which the dog was placed inside a crate (24"×30") secured in the back of the transport vehicle (cargo van). The crate consists of mesh wire sides and a plastic floor covered with a rubber mat for traction. Three video cameras were mounted within the vehicle in order to record the behaviour of the dog from various angles (front, back and one side view). The 10-minute session commenced when the vehicle began moving. The course taken for each session was identical and the driver attempted to keep the speed of each session consistent, as well as other factors such as noise and temperature. Two technicians were present in the vehicle. One person operated the van and the second person monitored the animal.

Animals were monitored throughout the car ride by a designated technician who manually recorded salivation, vomiting, urination, defecation and vocalization frequency. Continuous video recordings were saved for future behavioural assessments. The video recordings were analyzed following the car ride. Body position (duration of standing vs. lying down) and lip licking frequency were recorded by key press. The presence of panting, salivating, yawning and escape attempts behaviours were also documented.

Continuous heart rate data were collected from each subject for the duration of each car rides using the Polar H7 heart rate sensor and chest strap. Prior to their scheduled ride, the chest strap was placed on the dog just behind the forelimbs. The sensor was oriented at the side of the chest where a small patch of fur had been shaved. Contact gel was used to improve connectivity of the sensor. The heart rate chest strap was placed on the dog 5-6 minutes prior to the test time. The dog was acclimated to the strap for a minimum of two minutes, followed by three minutes of heart rate recording while the dog was at rest before the dog was placed in the vehicle. Once testing has completed, the heart rate monitor was removed from the subject. A baseline heart rate was also collected by stethoscope immediately prior to dosing.

Blood was collected for health profiling on day −8 and 2 mL and was placed into each a potassium oxalate/sodium fluoride, SST and K2EDTA tube. Whole blood collections for the purpose of cortisol and cannabidiol analysis were taken on eight occasions. Four (4) ml blood samples were collected from a suitable vein according to standard operating procedure for baseline 1 day prior to the car and 10 minutes (±2 minutes) after each car ride for cortisol and cannabidiol analysis. Prior to the baseline sample, subjects were placed in a quiet metabolic cage for 30 minutes (±2 minutes) for a more accurate reading of cortisol at rest. Two (2) ml blood were placed into a 2 ml SST tube and allowed to set until clotted. Serum was separated by centrifugation (2800-3200 rpm for 10 minutes at room temperature) and removed into a new serum blood tube. One aliquot of serum (0.5 ml) was placed into a cryovial and stored at approximately −80° C. for future analysis as necessary. Tubes were stored at 2-8° C. until picked up by Antech Diagnostics on the same day as the cortisol collection. For cannabidiol analysis, 2 mL of whole blood was collected at the respective time points at baseline and after drug administration and transferred into a K2EDTA tube and inverted gently. Samples were centrifuged at 3000 rpm for 10 minutes at 4° C. Plasma was separated evenly into two cryovials and stored at −20° C. until transferred to −80° C. Samples were analysed by mass spectrometry for the presence of cannabidiols and in particular CBD.

Dosing regimen (dose(s), frequency, and duration): Animals received either the test article or placebo, at 4 hours±10 minutes prior to car ride testing. The test article was diluted to the correct concentration (4, 12 or 25 mg/mL) with an appropriate volume of MCT oil to a final volume of 4 mL. The test article was administered with attention to complete delivery and retention of the entire intended dose according to standard operating procedure, briefly: i) The dog's head was tilted upward; ii) The dosing syringe was inserted into the corner of the mouth, angled toward the back of the mouth; iii) The 4 mL contents of the syringe was administered; iv) The head was kept raised for a few seconds to ensure retention of the dose, swallowing may be encouraged by rubbing the ventral neck area; v) A 10 mL water flush was administered via syringe to facilitate esophageal transfer of the article; vi) The dog was returned to its cage; vii) Dosing always involve no fewer than two people.

All analyses were performed using SAS V 9.3 (Cary, N.C.). A significance threshold of 0.05 was used. Multiple comparisons were adjusted for using Tukey's test. Histograms and probability plots were for each group and for each variable. Multiple normality tests including Shapiro-Wilk were run. Linear mixed models (LMM) were used to test for order and sequence (first-order carry over effects) effects in the car ride activity response. The LMM included fixed factors for treatment (placebo, low, medium and high-dose), order, sequence, activity status (hyperactive or hypoactive) and a treatment by activity status interaction term and a random intercept for each dog. If there was a significant ($p<0.10$) interaction of activity status and treatment, then treatments were compared separately for each activity status. If sequence and/or order effects had $p>0.10$ then they were removed from the LMM for testing of treatment effects. An additional contrast was also made comparing placebo to combined low, medium and high-dose values. LMMs was also used to test for order and sequence (first-order carry over effects) effects in post-car ride cortisol, heart-rate and global anxiety scores. The LMM included fixed factors for treatment (placebo, low, medium and high-dose), order, sequence and a random intercept for each dog. If sequence and/or order effects had $p>0.10$ then they were removed from the LMM for testing of treatment effects. An additional contrast was made comparing placebo to combined low, medium and high-dose values.

Example 2—Assessment of CBD and 7-COOH-CBD Levels Pre-Car Ride and Post-Car Ride Post-car ride CBD levels were analyzed as a function of Dose using non-parametric analysis of variance. The analysis revealed a highly significant dose effect ($p=0.0000$). FIG. 1 shows the data plotted as a function of dose.

Figure 2:
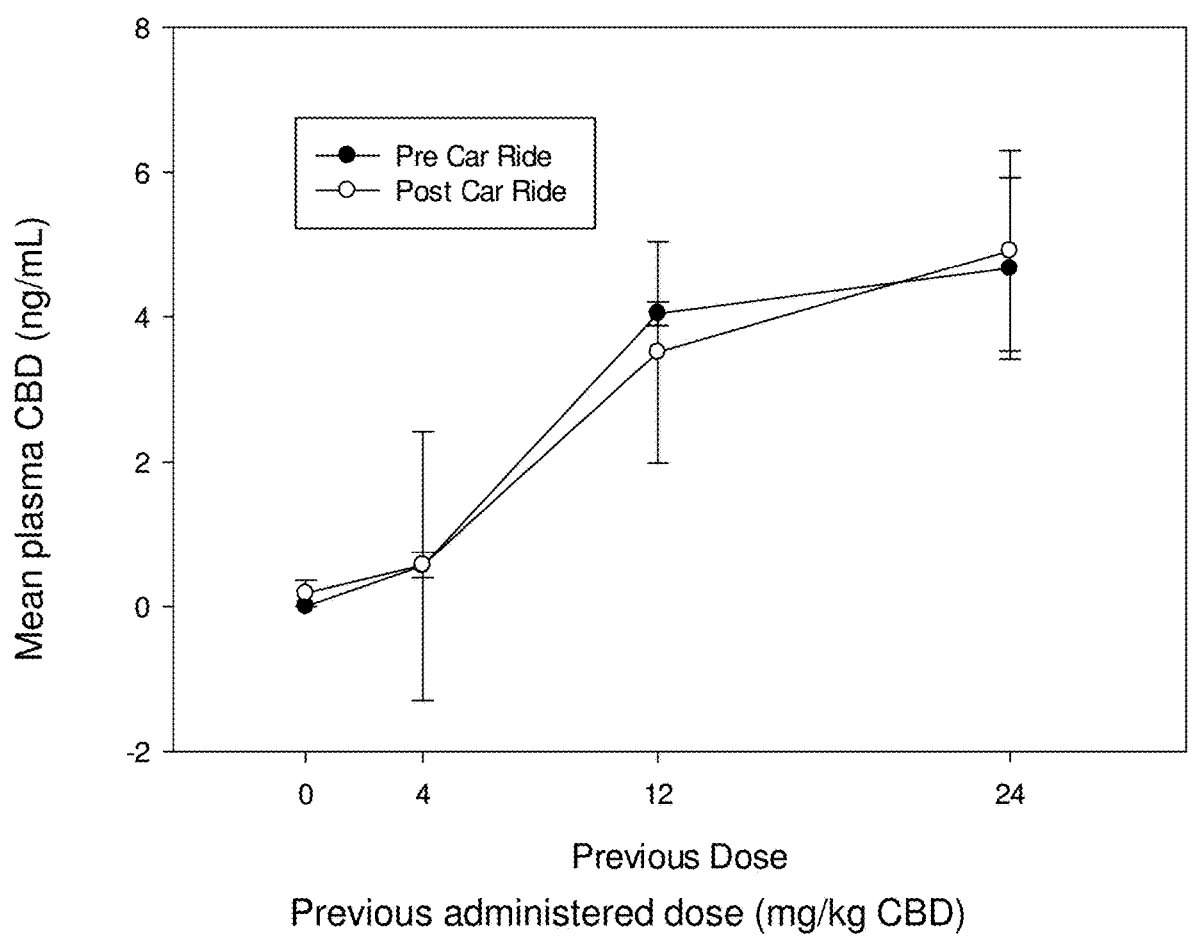
FIG. 2 is a graph showing the pre- and post-car ride levels of CBD in tested dogs as a Function of Previous Dose. Subjects were assigned a score of 0.29 if the reading was indicated at BLD, and scores of 0 if there was no peak.

Pre-car ride CBD levels were analyzed as a function of previous Dose using non-parametric analysis of variance. Detectable levels of CBD were obtained from several of the animals under the placebo control condition, but not at baseline. To assess the effect of previous dosing, compared placebo level were examined with previous dose level using a repeated measures ANOVA, with time of dosing as a within subject variable and previous dosing level as a between subject variable. Previous dose effect was significant at the 0.02 level (FIG. 2).

Figure 3:
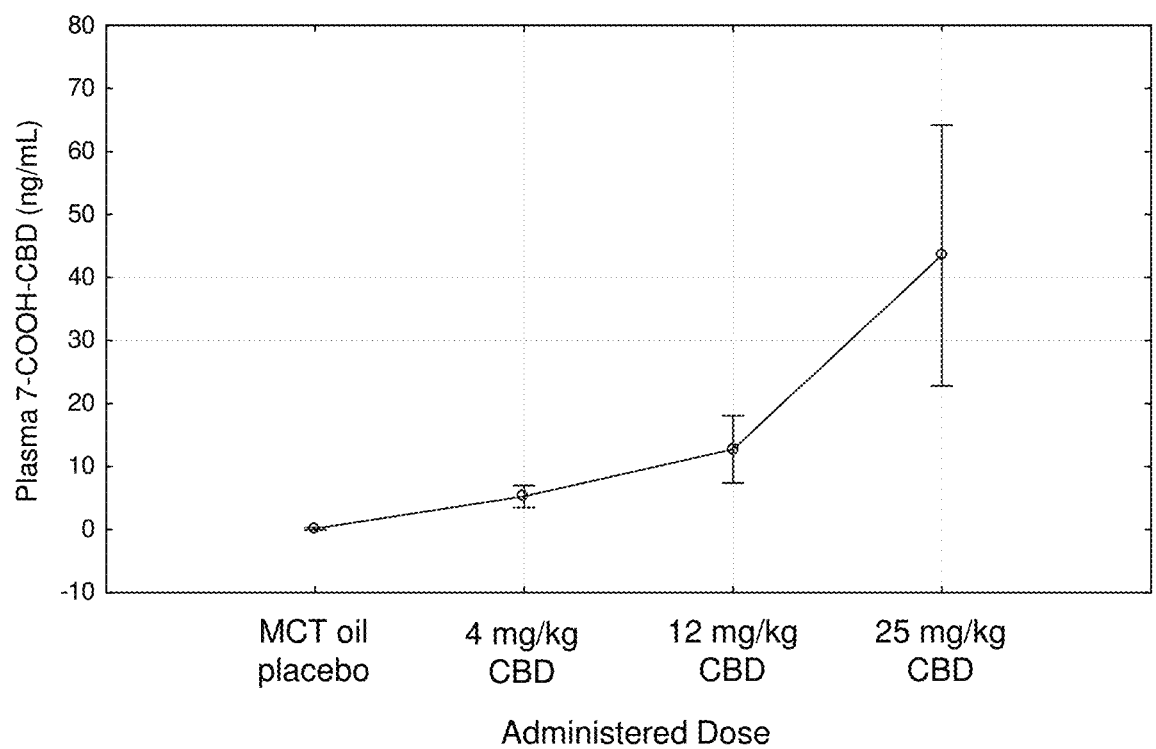
FIG. 3 is a graph showing concentration of 7-COOH-CBD in the tested dogs as a function of dose; current effect $F(3, 45)=16.402$; $p=0.00000$.

7-COOH-CBD levels were compared across the 4 dose levels using a repeated measures ANOVA, which revealed a highly significant effect of dose. FIG. 3 shows that the dose response range mimicked that of CBD. The correlations between CBD and 7-COOH-CBD was also evaluated, the results are presented in Table 4 which shows that the correlations were highly significant at each dose range. Although, the Significant correlation under the placebo condition is also statistically significant, this result reflects data from only two animals, both of which showed both moderate levels of CBD and detectable levels of 7-COOH-CBD.

Example 3—Assessment of Heart Rate Pre- and Post-Car Ride

The analysis of the heart rate data distinguished three distinct time intervals: (1) the pre-test interval which was calculated by calculating the mean heart rate over the 30 seconds interval immediately preceding the start of the car ride; (2) the mean over the first five minutes of the car ride and (3) the mean over minutes 5-10 of the car ride. The data used in the analyses was organized by both phase and treatment. The data were first analyzed for order effects. Repeated measures ANOVA were performed with both time measure (pre, post 1 and post 2) and test phase as within subject variables and sex as a between subject variable. Pos-hoc comparisons were then performed post-hoc comparisons of all means vs each other using the Tukey Multiple comparison Test.

Figure 4:
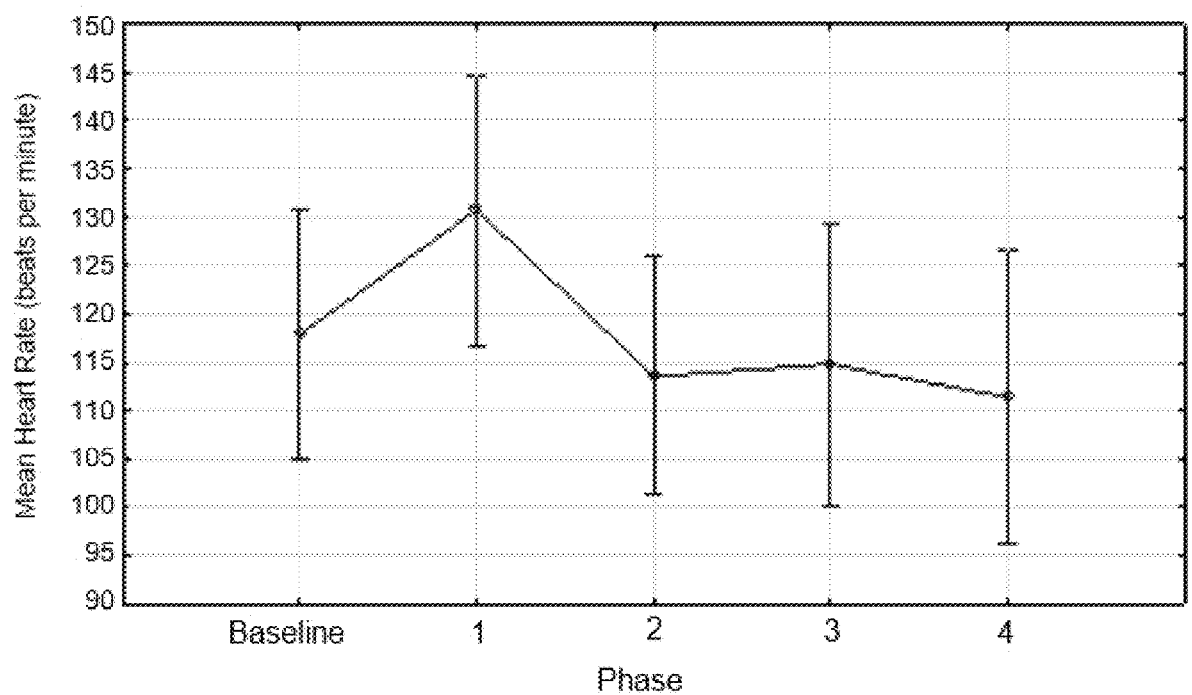
FIG. 4 is a graph showing mean heart rate in tested dogs as a function of test phase; wherein: 1: baseline; 2: treatment phase 1, 3: treatment phase 2, 4: treatment phase 3, and 5: treatment phase 4; current effect $F(4, 52)=3.9253$; $p=0.00737$.

The analysis revealed statistically significant main effects of test phase and time interval, as well as a statistically significant interaction between test phase and time interval. FIG. 4 shows that the primary origin of the significant phase effect was due to a higher overall mean heart rate during the first test phase. Phase 1 was significantly higher than baseline as well as test phase 2, 3 and 4.

Figure 5:
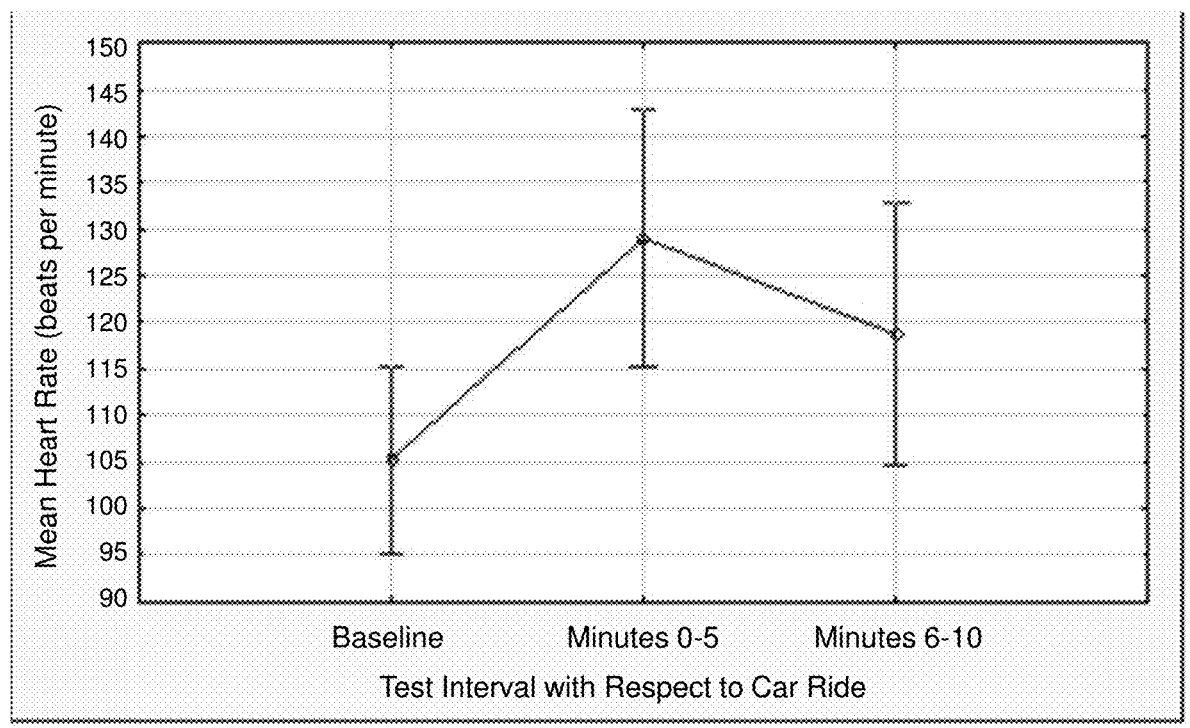
FIG. 5 is a graph showing mean heart rate in tested dogs as a function of time interval; current effect F(2, 26)=16.641; p=0.00002.
Figure 6:
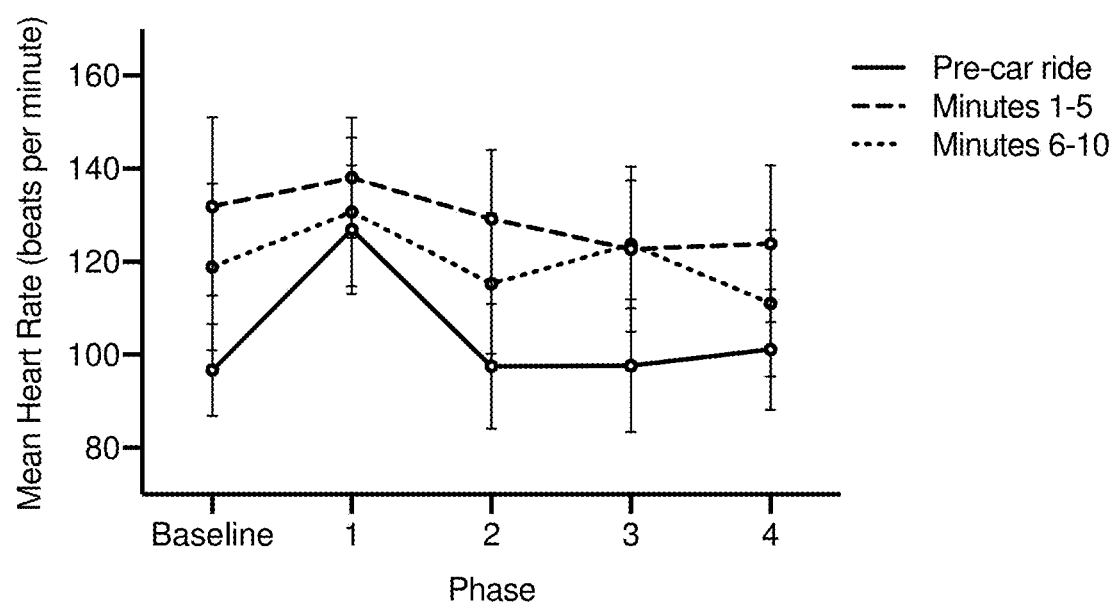
FIG. 6 is a graph showing mean heart rate in tested dogs as a function of treatment phase and time period.
Figure 7:
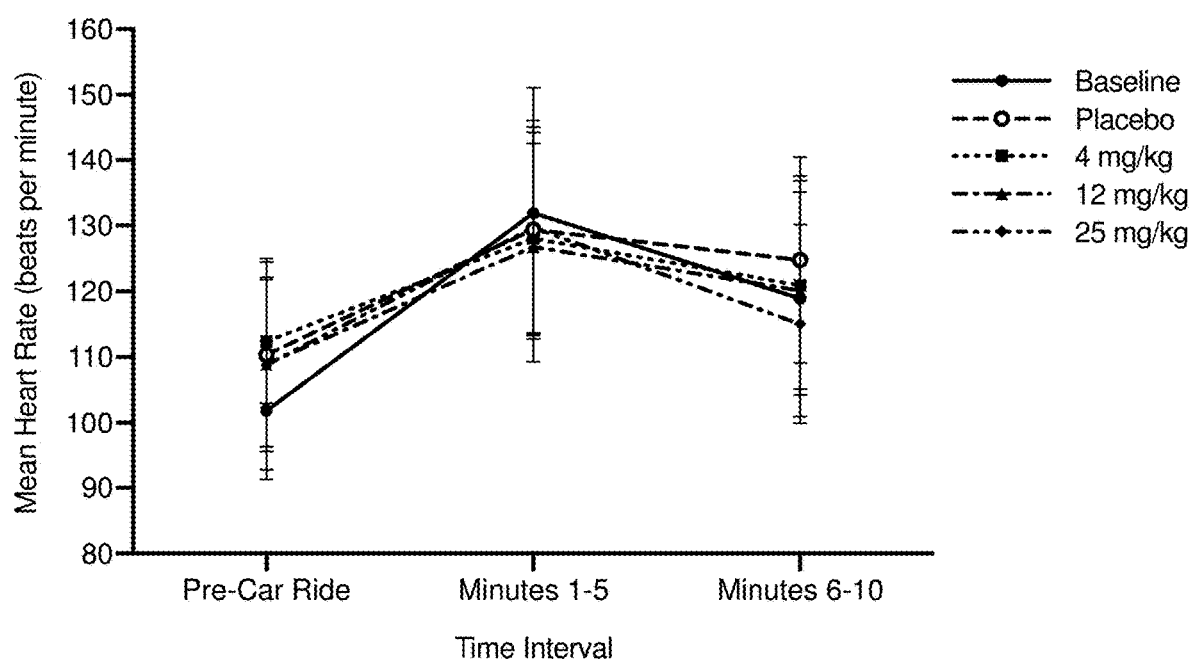
FIG. 7 is a graph showing mean heart rate in tested dogs as a function of treatment and time period; wherein: Treatment 1: Baseline; Treatment 2: Placebo; Treatment 3: 4 mg/kg dose CBD; Treatment 4: 12 mg/kg CBD; Dose and Treatment 5: 25 mg/kg dose CBD.

The origins of the significant effect of time period is shown in FIG. 5, which illustrates that the lowest mean heart rate was recorded over the pre-test period and highest was measured during the first five minutes of the car ride. The results of the post-hoc Tukey analysis revealed that each of the three test periods differed significantly from each other. Finally, FIG. 6 shows that the significant interaction between time interval and phase was largely driven by a higher heart rate during the pre-test period during the first treatment phase. The treatment data were first analyzed with a Repeated Measures ANOVA with treatment (baseline, placebo, 4 mg/kg, 12 mg/kg and 25 mg/kg) and time period as within subject variables and sex as a between subject variable (FIG. 7). The results of the analyses revealed a significant effect of time period, and no other significant main effects or interactions. The heart rate results, like the cortisol data, were also validated as a measure of stress, with consistently significant increases in heart rate occurring during the car ride, when compared to pre-car ride levels. Furthermore, heart-rate levels from minutes 6-10 were significantly lower than heart rate levels from minutes 1 to 5. Thus the heart rate increase falls off over time, suggesting some degree of adaptation. We also found a significant difference between test phases. However, this was driven by an increase in heart during baseline testing in the first treatment phase only, and there were no other consistent changes over the course of testing.

Example 4—Evaluation of Anxiolytic Properties of CBD

The effects of administration of CBD on increased serum cortisol levels triggered in response to anxiety were evalu-

TABLE 4

Figure 8:
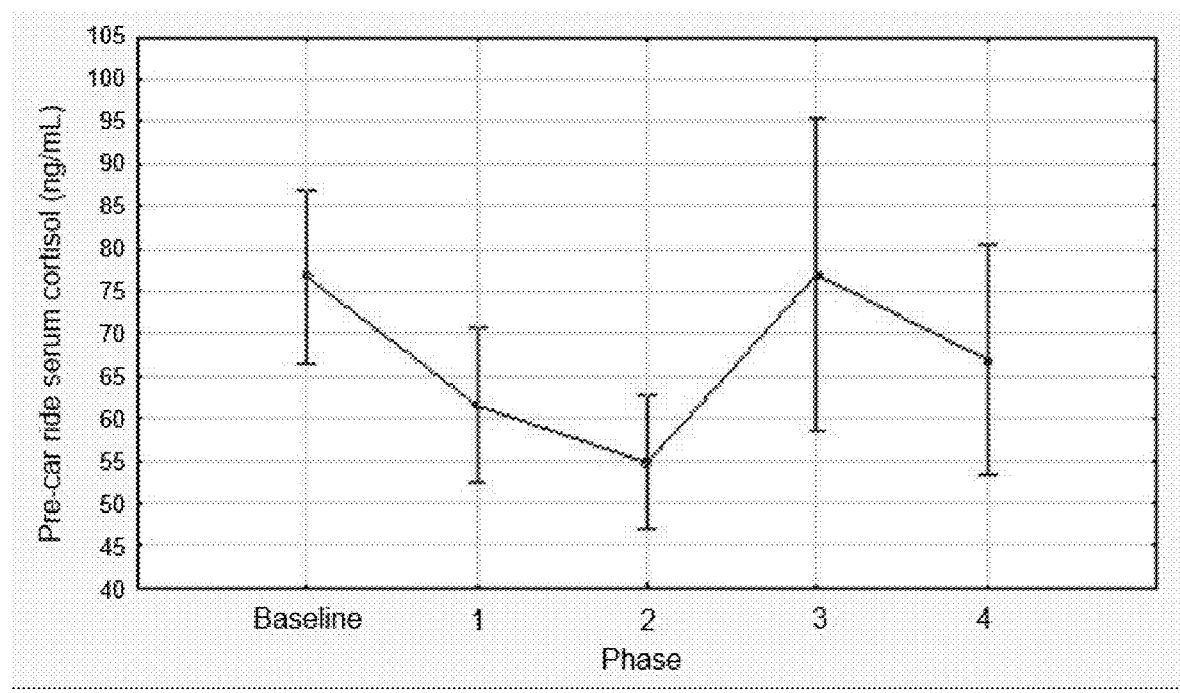
FIG. 8 is a graph showing pre-car ride blood cortisol level in tested dogs as a function of Phase; current effect F(4, 60)=4.2298; p=0.00441.

| Correlation between 7-COOH-CBD and CBD | | | | |
|---|---|---|---|---|
| | CBD Placebo Post-car ride | CBD Post-car ride 4 mg/kg | CBD Post-car ride 12 mg/kg | CBD Post-car ride 25 mg/kg |
| 7-COOH CBD | 0.684427 | −0.034265 | −0.258932 | −0.227102 |
| 7-COOH-CBD 4 mg/kg | −0.248755 | 0.783065 | 0.628228 | 0.200971 |
| 7-COOH-CBD 12 mg/kg post | −0.263486 | 0.469330 | 0.716165 | 0.170598 |
| 7-COOH-CBD 25 mg/kg | −0.401542 | 0.479918 | 0.590406 | 0.903646 | ated according to the study design outlined in Example 1. The data obtained were first analyzed for order effects which were done by separately comparing pre-car ride cortisol, post-car ride cortisol and a difference score was calculated by subtracting pre-car ride cortisol from post-car ride cortisol and each time point, independent of treatment. All analyses were first performed using repeated measures ANOVA. Pos-hoc comparisons were performed post-hoc comparisons of all means vs. each other using the Tukey Multiple comparison Test. The results of the ANOVA comparing pre-car ride means at all test phases revealed a significant order effect (p=0.004). FIG. 8 shows that the significant result reflected a lower pre-car ride cortisol response during Phase 2.

Figure 9:
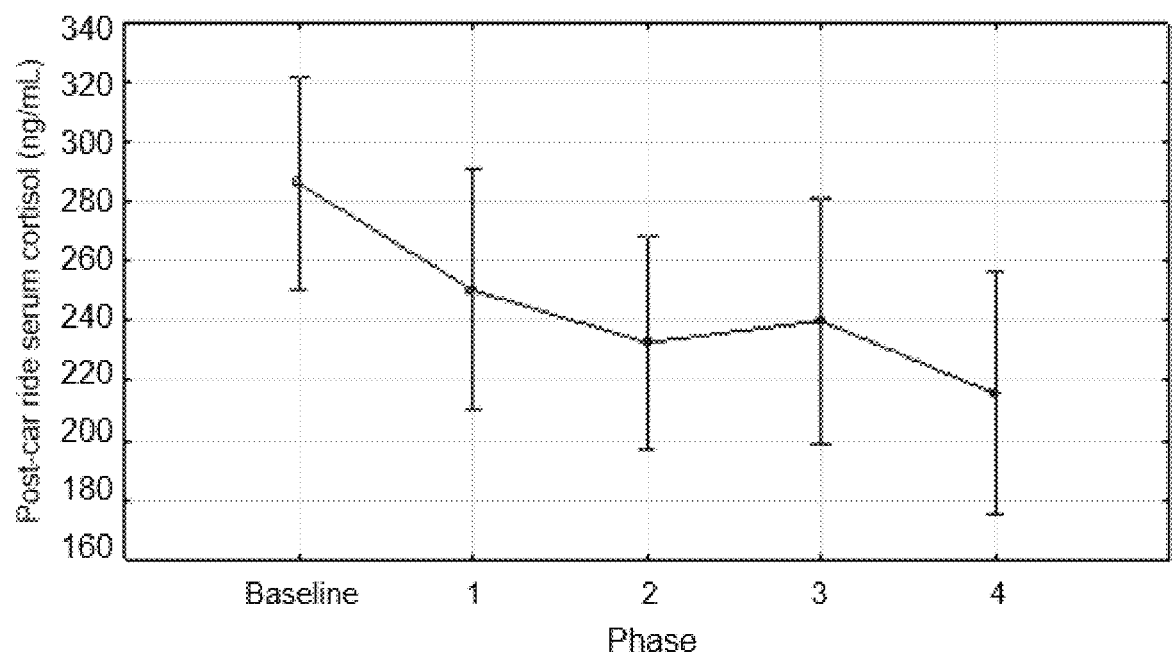
FIG. 9 is a graph showing post-car ride blood cortisol level in tested dogs as a function of Phase; current effect F(4, 60)=8.2356; p=0.00002.
Figure 10:
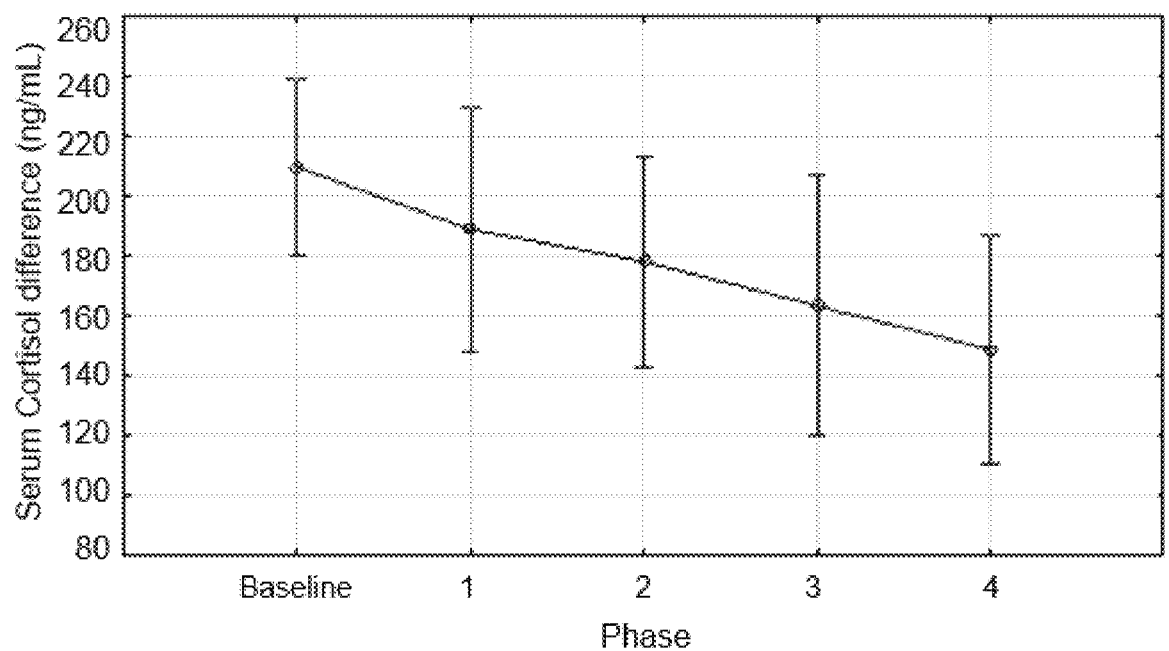
FIG. 10 is a graph showing the difference between pre-car ride and post-car ride cortisol level in tested dogs as indicated as mean difference scores as a function of test phase; current effect F(4, 60)=5.0272; p=0.00146.
Figure 11:
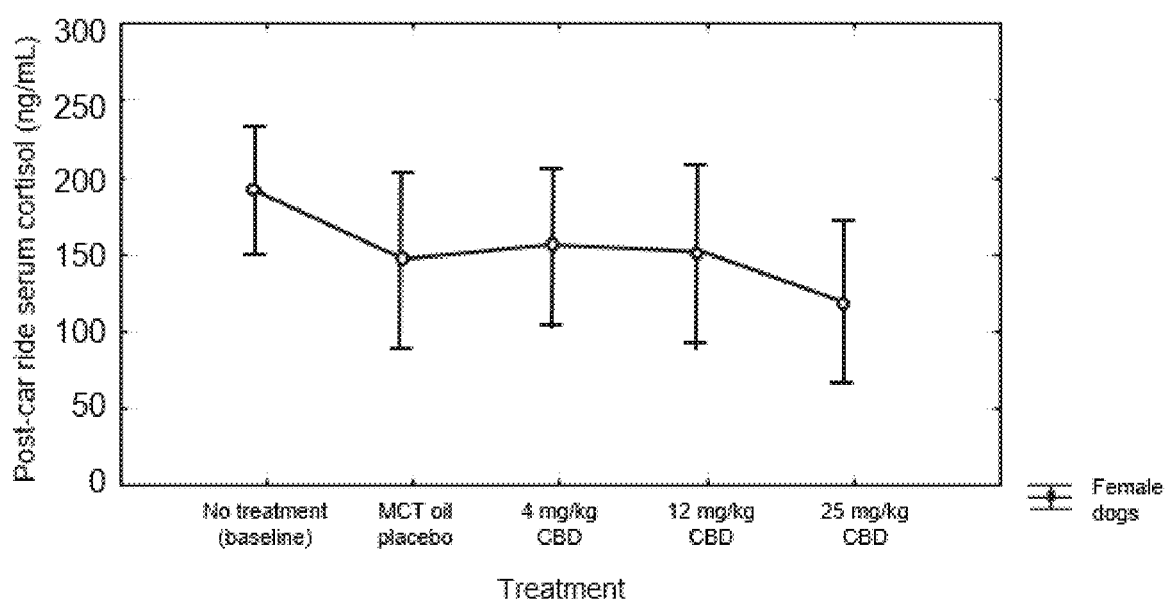
FIG. 11 is a graph showing post-car ride cortisol levels in female dogs tested as a function of treatment with CBD; current effect F(4, 56)=0.69686; p=0.59733.

The results of the analysis of the post-treatment day also revealed a statistically significant effect of Phase (p=0.0000). FIG. 9 shows a progressive decrease in cortisol. Marginally significant differences were found between baseline and test phase 2, and between test phase two and test phase 5. The results of the repeated measures ANOVA revealed a statistically significant effect of test phase (p=0.0015). FIG. 10 shows that this reflects progressive decrease in the difference between pre-car ride and post-car ride cortisol levels. The data was first analyzed using repeated measures ANOVA, in which both time of sample (pre-car ride vs. post-car ride cortisol levels) and treatment served as within subject variables. The results of the analyses revealed statistically significant main effects of treatment. The treatment effect was driven by differences between post-car ride cortisol at baseline when compared with post-car ride cortisol during the test phases (at all treatment levels). FIG. 11 shows that female dogs showed a decrease in cortisol levels in responses to CBD administration.

The cortisol results strongly validate the car ride model as a model of induced anxiety and stress, as evidenced by a consistent and marked increase over baseline levels in serum cortisol levels in the tested dog subjects. In addition, correlations between different test arms indicate that there are consistent individual differences in the magnitude of the cortisol response between subjects. Statistically significant differences were found between Phases, which appeared linear, suggesting consistent decreases in the cortisol response with repeated exposure. Finally, a cortisol response was observed in female dog subjects upon administration of CBD.

Overall, the medium and high dose treatments, which differed significantly from baseline, were more effective in reducing the cortisol response than the placebo and low dose treatments. This data shows that administration of CBD decreases the elevated cortisol levels induced during stress and anxiety and suggest a role for CBD in the treatment of anxiety and stress in animals such as dogs.

Example 5—Assessment of the Anxiolytic Properties of a Cannabinoid Formulation in Dogs Using a Noise-Induced Model for Fear and Anxiety A Noise-Induced Model for fear and anxiety was used to assess the anxiolytic properties of a cannabidiol formulation on dog subjects. An objective of this study is to determine the anxiolytic effectiveness of an orally dosed CBD enriched cannabinoid formulation at three dose levels (25 mg/kg, 12 mg/kg, and 4 mg/kg) as compared to a placebo control in a noise-induced model of fear and anxiety.

A preliminary health screen including veterinary examinations and CBC/clinical chemistry blood work analysis was first used to select thirty-two (32) Beagle dogs for the Baseline Screening phase of this study. The 16 of these 32 animals that showed the greatest evidence of stress (based on serum cortisol and behavioural response) in a baseline simulated thunderstorm task were then enrolled in the treatment phase. A four-arm Williams design was used, with four treatment groups of 4 animals per group. Subjects were allocated to the treatment groups (n=4) balanced for sex, serum cortisol, and behavioural (activity) response. On Days 4, 11, 18, and 25 (n=16), dogs were tested on the thunderstorm procedure after administration of one of three dose levels of test article or placebo. Anxiety was assessed by both live monitoring of specific behaviours and through post-trial monitoring of recorded video files, by continuous recording of heart rate during the test, and by analyzing serum cortisol levels after the test. Subjects were dosed once during each arm of the study, approximately 4 hours prior to the thunderstorm test. Blood was taken twice during each arm of the study including baseline phase; once for the purpose of determining resting cortisol levels, collected two days before thunderstorm procedures, and once for the purpose of determining post-thunderstorm cortisol levels as well as blood levels CBD and 7-COOH-CBD, collected 5 minutes (±2 minutes) following the test. Both blood collections were taken at about same time of day. There was a 6-day washout period between treatment days for all subjects. The order of testing was balanced and is shown in Table 7.

TABLE 7

Treatment as a function of Group and Cycle

| Sequence | # of Subjects | Cycle 1 (Days 1-4) | | Cycle 2 (Days 8-11) | | Cycle 3 (Days 15-18) | | Cycle 4 (Days 22-25) |
|---|---|---|---|---|---|---|---|---|
| A | 4 | 25 mg/kg | 6 Day | 12 mg/kg | 6 Day | Placebo | 6 Day | 4 mg/kg |
| B | 4 | 12 mg/kg | Wash | 4 mg/kg | Wash | 25 mg/kg | Wash | Placebo |
| C | 4 | 4 mg/kg | Out | Placebo | Out | 12 mg/kg | Out | 25 mg/kg |
| D | 4 | Placebo | | 25 mg/kg | | 4 mg/kg | | 12 mg/kg |

On the day of testing, each group received a single dose of their assigned treatment according to Table 7 followed by a 6-day washout period prior to the next assessment Animals were dosed 4 hours (±10 minutes) prior to each thunderstorm assessment, at the same time of day on each dosing day. Subjects received either placebo (MCT oil) or CBD extract diluted to the correct concentration of either 4, 12 or 25 mg/kg with appropriate volume of MCT oil to a final volume of 4 mL for each dose. The test article was administered orally by syringe with attention to complete delivery and retention of the intended dose according to standard operating procedures. In the event that a subject vomited or regurgitated within the first 30 minutes of administration, the product was re-administered and time of re-dose was recorded.

Whole blood collections for the purpose of cortisol and cannabinoid analysis were taken on 10 occasions. Approximately 4 mL of blood was collected from a suitable vein according to standard operating procedure at each time point for cortisol measures two days prior to each thunderstorm test and 5 minutes (±2 minutes) after each thunderstorm test. Prior to each pre-thunderstorm test blood collection, subjects were placed under metabolic rest for 30 minutes (±2 minutes) to determine an accurate resting cortisol level. Prior to each post-test collection, subjects were given approximately 5 minutes (±2 minutes) of metabolic rest following the test. Two (2) mL of whole blood was placed into an SST tube and allowed to clot before centrifugation at 2800-3200 rpm for 10 minutes at room temperature. Tubes were stored at 2-8° C. until analysis. For cannabinoid analysis, 2 mL of whole blood was collected at baseline, at the pre-thunder test timepoint as well as 5 minutes (±2 minutes) following each thunderstorm procedure, transferred into a $K_2$EDTA tube and inverted gently. Samples were centrifuged at 3000 rpm for 10 minutes at 4° C., after which plasma was equally aliquoted into two cryovials.

Open field Testing occurred during baseline procedures (Day −6 and −4) and treatment phase on study Day 3, 5, 10, 12, 17, 19, 24 and 26. The open field test was performed in a specially constructed test room (approximately 8×9 feet) that included three cameras for recording movement, one of which also recorded sound. Prior to entry of each animal, the room was cleaned to prevent previous animal odours from affecting test performance. Subjects were allowed to freely explore the room over a 9-minute period during which behaviour was recorded for analysis of the following parameters: i) Distance travelled (m); and ii) Inactivity frequency and duration (s). All behavioural parameters were measured using Ethovision XT®. This software was calibrated to the measurements of the room and could therefore measure distance travelled automatically. The other customized variables were recorded by a trained observer via key press while watching the animal over video feed. In addition, a video file of each session was saved for archiving purposes.

The thunderstorm test was performed on Study Day −5, 4, 11, 18, and 25; this took place in the open field arena. During the 9-minute task, the first three minutes was designated as the pre-thunder interval, during which the dogs were allowed to freely explore the room in the absence of any external stimuli. During minutes 4-6 (thunder interval) a recorded thunderstorm track was played over a stereo system at approximately 105 dB. Animal behaviour was audio and video recorded for a total of 9 minutes and the following parameters assessed:

1. Distance travelled (m): the distance the animal moves within the room will be tracked and recorded in meters.

2. Inactivity frequency and duration (s): recorded if the animal is sitting, lying down, or not exhibiting any directed or overt behavior. All other behaviours were considered "active" behaviours.

No stimuli were provided over the last three minutes (minutes 7-9). All behavioural parameters were measured as described for the open field test. Video files of each session were recorded to DVD and archived with the study files. All observed anxiety behaviour was scored for each 3 minute segment each thunderstorm test (days −5, 4, 11, 18, 25) for each 3 minute segment (pre, during and post) and for the conditioned anxiety open field test (days −4, 5, 12, 19, 26) for the first 3 minute segment (conditioned anxiety) by the same trained technician for the course of the study, blinded to treatment conditions, using an anxiety scale developed by Dr. Gary Landsberg. This scale provides measures of active and passive fear and anxiety. Global anxiety, which is an overall assessment that takes into consideration both frequency and intensity of positive and negative anxiety. Positive (active) anxiety, including the following behaviours: startle; bolting; scanning; actively retreating, aimless pacing and circling (as opposed to normal exploration); digging, scratching or climbing walls; and vocalization Passive (reactive) anxiety, including the following behaviours: panting; lip-licking; shaking; yawning; salivating; cowering; tail tucking; freeze near wall; vigilance; and general inactivity in response to thunder (as opposed to resting).

Figure 12:
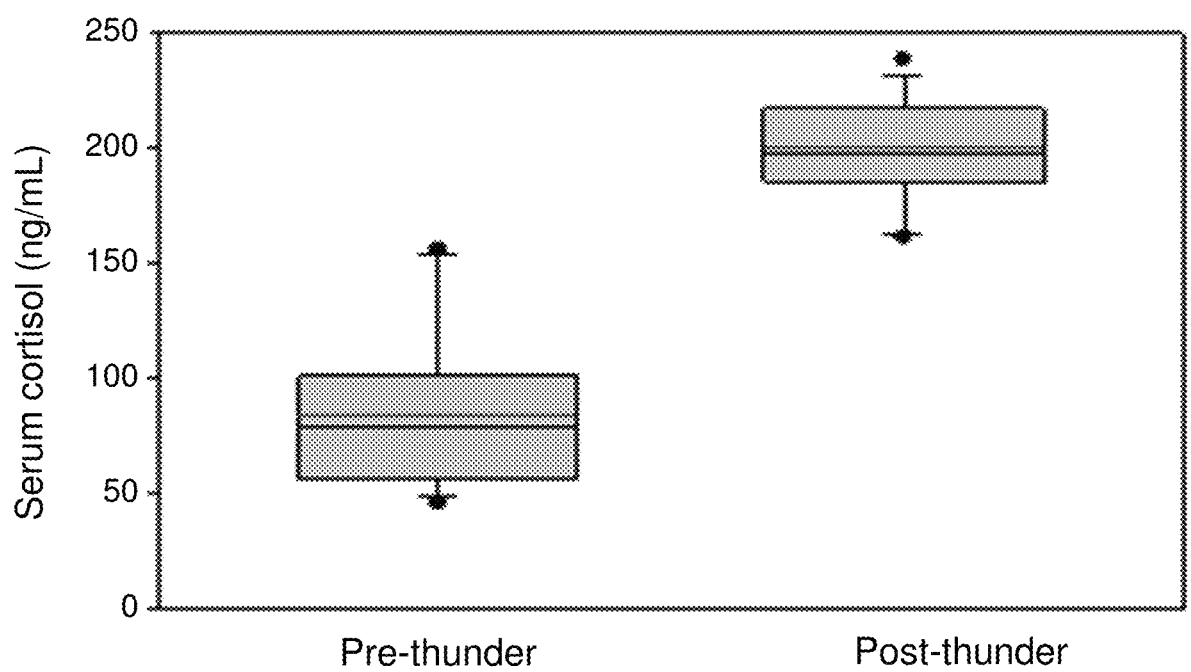
FIG. 12 is a graph showing a Box and Whiskers Plot of Pre- and Post-Thunder levels of Serum Cortisol in tested dogs. The boundaries of the box show the $25^{th}$ and $75^{th}$ quartiles. The black horizontal line represents the median and the mean is represented by the red horizontal line.

At baseline, all subjects showed a post-thunder increase in blood cortisol with differences ranging from 23 to 213 percent. FIG. 12 shows a box and whiskers plot of the pre- and post-thunder baseline data.

Figure 13:
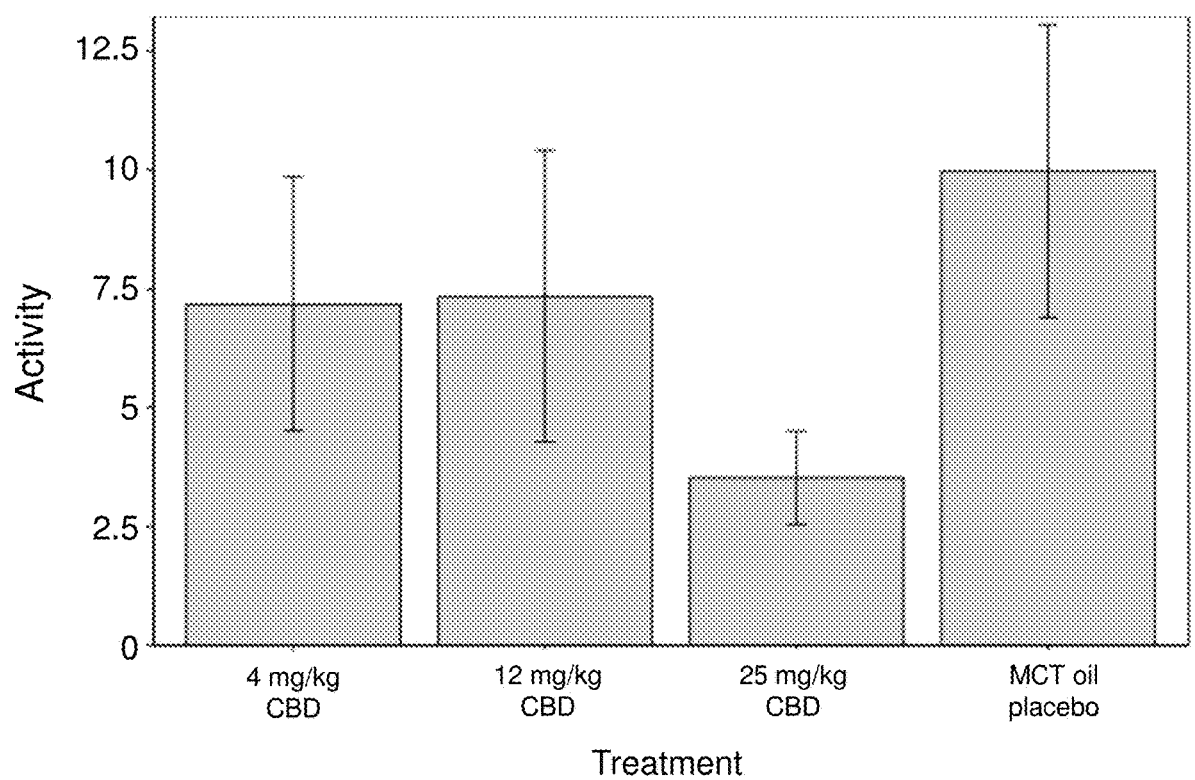
FIG. 13 is a graph showing distance travelled (m) by tested dogs during thunder minutes 7-9 across treatment groups.
Figure 14:
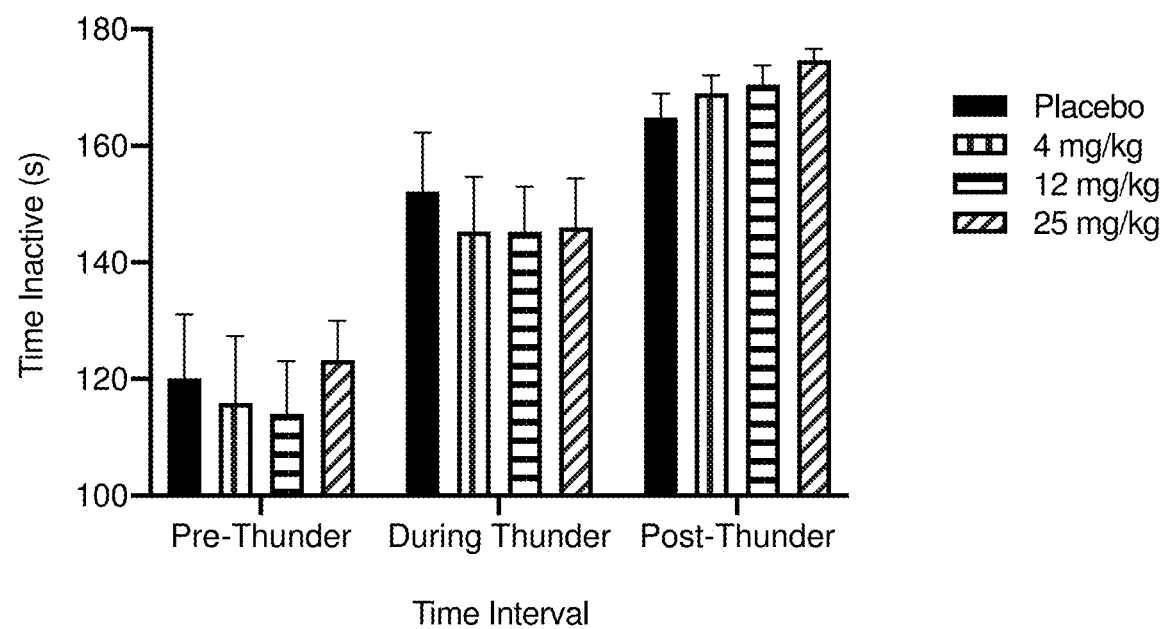
FIG. 14 is a graph showing inactivity of the tested dogs as a function of time of test (pre-, during, and post-thunder) and dose of CBD administered to the tested dogs.

The effect of CBD on Behavioral Response to Thunder was measured. Distanced travelled was significantly larger with placebo than 25 mg/kg (p=0.0445, LMM with treatment and order) (FIG. 13) and inactivity frequency was significantly smaller with placebo than 25 mg/kg (p=0.0245, LMM with treatment and order) post-thunder. There were no significant differences in activity during minutes 1-3 during conditioned anxiety testing. There were 8 out of 12 activity variables with p<0.10 for order effects. Inactivity was analyzed using repeated measures ANOVA with time of test (pre-thunder, thunder, and post-thunder) as within subject variable and both sex and dose as between subject variables. Time of test was highly significant (p=0.000) with no other significant main effects or interactions. The p value for the dose effect was 0.762. As shown in FIG. 14, inactivity increased progressively from the first to the last three minutes.

Figure 15:
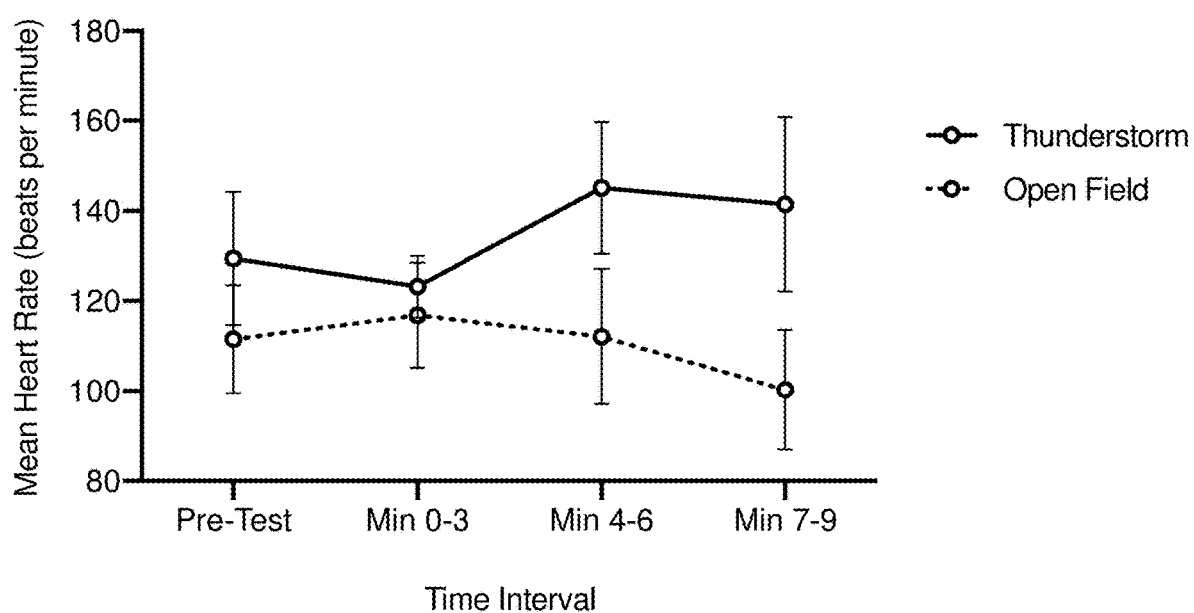
FIG. 15 is a graph showing mean heart rate in tested dogs as a function of time interval (1=prior to placement in test room; 2=minutes 1-3; 3=minutes 4-6 and 4=minutes 7-9) and presentation of thunder (thunderstorm vs control).

The effect of CBD on the Heart Rate in Response to Thunder was assessed. On each test, mean heart rates we calculated for the pre-test interval, minutes 1-3 in the test room, minutes 4-6 and minutes 7-9. To establish the validity of the heart measure, we first compared heart rate during open field with heart rate during the test condition using a repeated measures ANOVA. The results revealed a highly significant increase during the test condition (thunder vs open field; p=0.01) and a marginally significant interaction between test condition and time interval (p=0.083). FIG. 15 shows that heart rate increased over the pre-thunder levels in response to thunder, but not in the open field.

Figure 16:
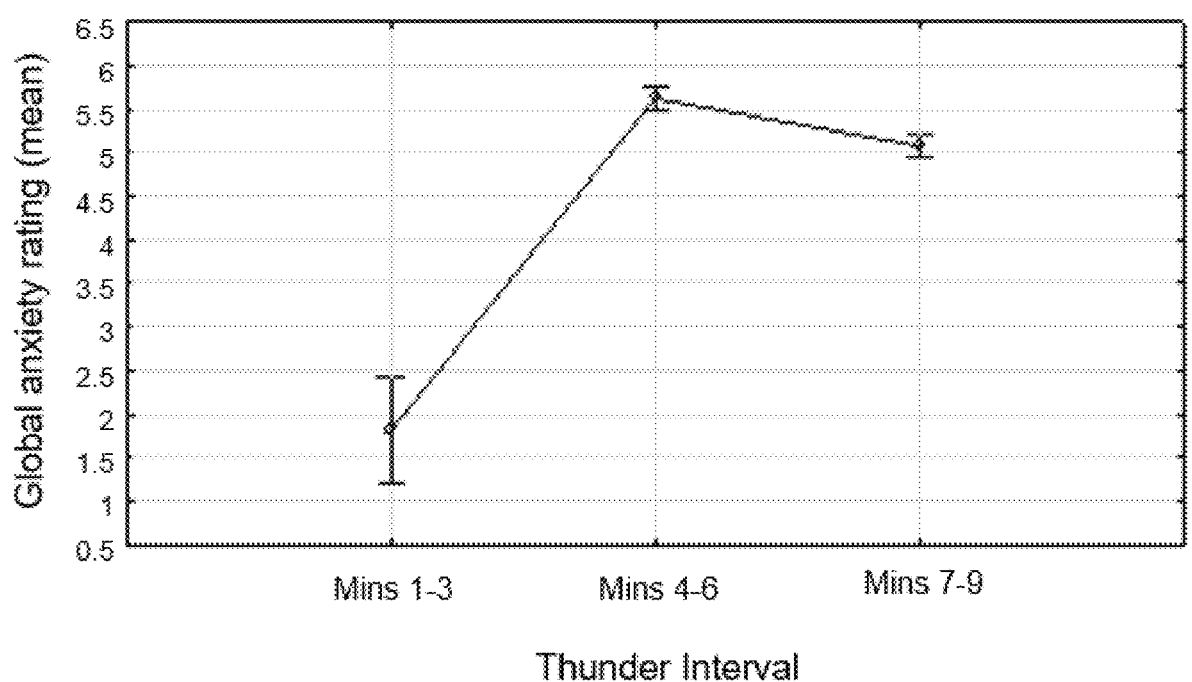
FIG. 16 is a graph showing mean global anxiety rating as a function of time relative to presentation of thunder on the baseline test; current effect F(2, 30)=168.40; p=0.0000.

The thunderstorm induced anxiety model was validated by first analyzing the baseline data using a one-way analysis of variance with time interval as the target variable. The analysis revealed a highly significant effect of thunder (p=0.000). FIG. 16 illustrates that the rated anxiety increased during the presentation of thunder and remained elevated during the post-thunder interval. The Tukey's test revealed significant differences between the baseline and both the thunder and post-thunder interval (p=0.000) for both comparisons. The comparison between thunder and post-thunder was marginally significant (p=0.053).

Example 7—Further Assessment of the Anxiolytic Properties of a Cannabinoid Formulation in Dogs Using Car-Ride Study and Noise-Induced Study Car-Ride Study:

a 10-minute car ride was used to induce fear and anxiety in adult Beagle dogs (n=16; 8 M, 8 F) ranging in age from 3.8 to 9.6 years and ranging in weight from 8.8 to 13.3 kg. The dogs were orally dosed with a single administration of placebo oil or CBD oil isolate (4, 12, or 25 mg CBD/kg) ~4 hours prior to the car ride. Observations of the animals were conducted over the entire 10-minute car ride (see Table 7 for outcomes measured). The 16 dogs (8 males, 8 females) were assigned to one of four groups (4 dogs/group). This was a crossover study and thus each of the four groups received every treatment (placebo, 4 mg/kg, 12 mg/kg, 25 mg/kg) albeit in a different order. Since there were four treatments (placebo and three different CBD doses), there were four phases in this study (Phases 1, 2, 3, 4). In the first phase of the study (Phase 1), four dogs received placebo, four dogs received 4 mg/kg, four dogs received 12 mg/kg, and four dogs received 25 mg/kg. After 7 days, the dogs in a specific treatment group switched to a different treatment, and this continued until all four groups received each treatment. Thus, each treatment group (4 dogs/group) received each of the four treatments and each dog experienced four car rides—i.e., a car ride after each of the four treatments.

An outcome measure of this study was the amount of time dogs spent "lying down" during the car ride, which is a behavior that is indicative of reduced anxiety. In Phase 1, the dogs received their first treatment and their first car ride following a particular treatment and thus this phase was not confounded by an "order effect" (i.e., the dogs had not yet adapted to the car ride). Using Phase 1 data:

- None of the dogs (i.e., 0 of 4 dogs) who received the placebo lay down over the 10-minute car ride;
- 50% of the dogs (i.e., 2 of 4 dogs) who received a CBD treatment of 4, 12, or 25 mg/kg lay down for the car ride for a duration that ranged from 3.8 min (about 40% of the car ride) to 8.4 min (about 80% of the car ride).

Figure 17:
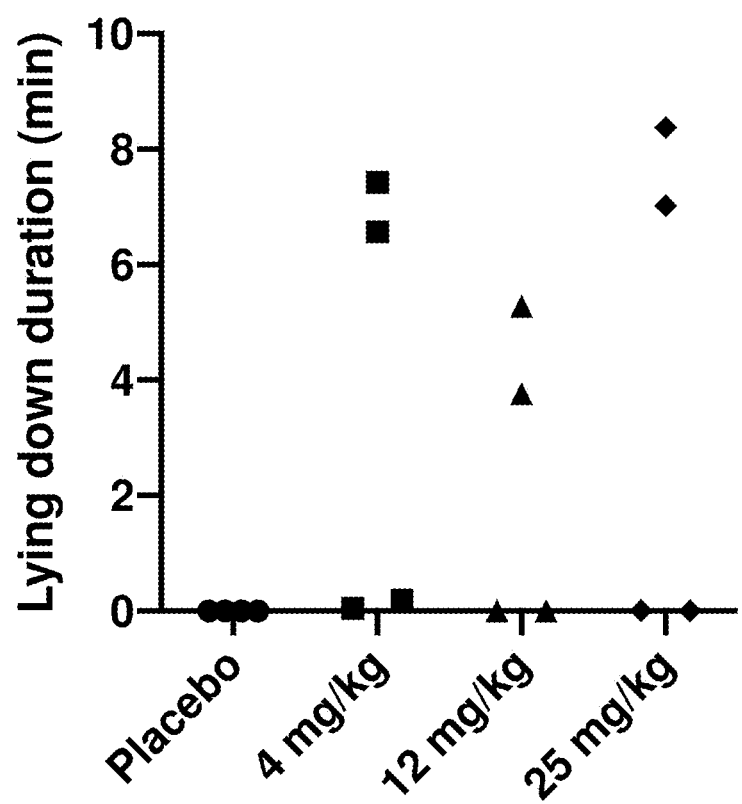
FIG. 17 is a graph showing the amount of time individual dogs lay down during a 10-minute car ride in Phase 1 of the study (n=4 dogs/treatment). Each data point corresponds to an individual dog.

The above findings, which are presented in FIG. 17, are suggestive of an effect of CBD (4, 12, or 25 mg/kg) on car ride anxiety. Moreover, of the six dogs across the CBD treatments who lay down during the car ride, 3 were female, and 3 were male, suggesting the potential anxiolytic effect of CBD may not differ across sexes. Overall, the study provides a signal for a calming effect of CBD (4, 12, 25 mg/kg) to an acute stressor (car ride)—treatment with CBD caused at least half of the adult Beagle dogs (6 of 12 dogs) to lie down for ~40% to 80% of the car ride duration; none of the 4 dogs in the placebo group lay down.

Thunderstorm Study:

a 3-minute thunderstorm noise was used to induce fear and anxiety in young Beagle dogs (n=16; 8 M, 8 F) aged 1.3 years and ranging in weight from 8.1 to 15.5 kg. The dogs were orally dosed with a single administration of placebo oil or CBD oil isolate (4, 12, or 25 mg CBD/kg) ~4 hours prior to the thunderstorm test. Similar to the car ride study, this was a crossover study. The 16 dogs (8 males, 8 females) were assigned to one of four groups (4 dogs/group) and each of the four groups received every treatment (placebo, 4 mg/kg, 12 mg/kg, 25 mg/kg) albeit in a different order. Thus, there were four phases in the study (Phases 1, 2, 3, 4) and during each phase each group of dogs received a different treatment. Over the course of the study, each dog experienced four thunderstorm sessions (i.e., a thunderstorm after each of the four treatments). Observations of the animals (Table 7) were conducted over a 9-minute session and analyses of the outcomes were divided into three time periods:

Pre-thunder: 3 minutes prior to initiation of the thunderstorm noise (minutes 1 to 3);

Thunder: 3 minutes during the thunderstorm noise (minutes 4 to 6); and,

Post-thunder: 3 minutes following the thunderstorm noise (minutes 7 to 9).

Figure 18:
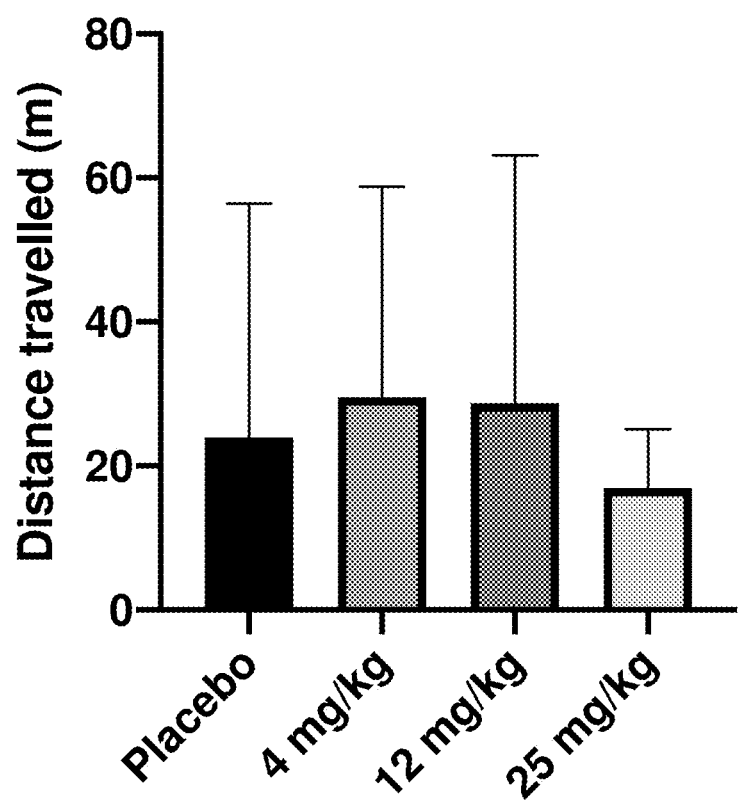
FIG. 18 is a graph showing the average distance (with standard deviation) travelled by the tested dogs in Phase 1 of the study during the 3-min thunderstorm noise (n=4 dogs/treatment).
Figure 19:
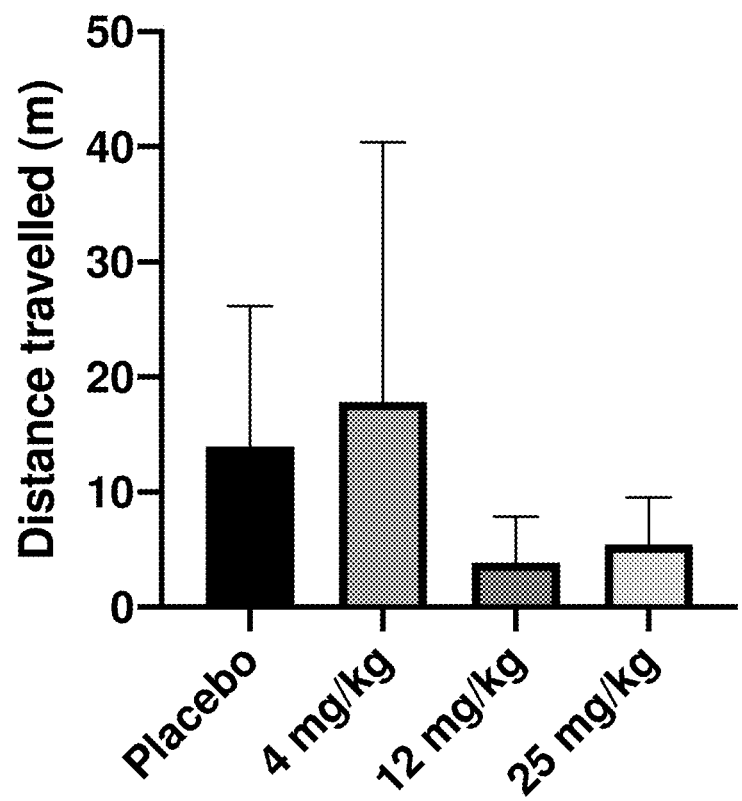
FIG. 19 is a graph showing the average distance (with standard deviation) travelled by the tested dogs in Phase 1 of the study during the 3-min post-thunder interval (n=4 dogs/treatment).

An outcome measure of this study was the amount of "distance", in meters (m), the dogs travelled during the thunderstorm session, with a greater distance travelled indicative of a higher level of anxiety. In Phase 1, the dogs received their first treatment and exposure to their first thunderstorm session following a particular treatment and thus this phase was not confounded by an "order effect" (i.e., the dogs had not yet adapted to the thunderstorm stressor). Using Phase 1 data and as indicated in FIG. 18 and FIG. 19, the following are noteworthy results:

During the 3-minute thunderstorm noise, the distance travelled by dogs receiving 25 mg/kg CBD (n=4 dogs) was reduced by 29% as compared to dogs receiving placebo (n=4 dogs) [mean±SD=17.0±8.1 m versus 24.0±32.5 m, respectively];

During the 3-minute post-thunder interval, the distance travelled by dogs receiving 12 mg/kg CBD (n=4 dogs) was reduced by 72% as compared to dogs receiving placebo (n=4 dogs) [mean±SD=3.9±3.9 m versus 14.0±12.2 m, respectively];

During the 3-minute post-thunder interval, the distance travelled by dogs receiving 25 mg/kg CBD (n=4 dogs) was reduced by 61% as compared to dogs receiving placebo (n=4 dogs) [mean±SD=5.5±4.0 m versus 14.0±12.2 m, respectively].

Figure 20:
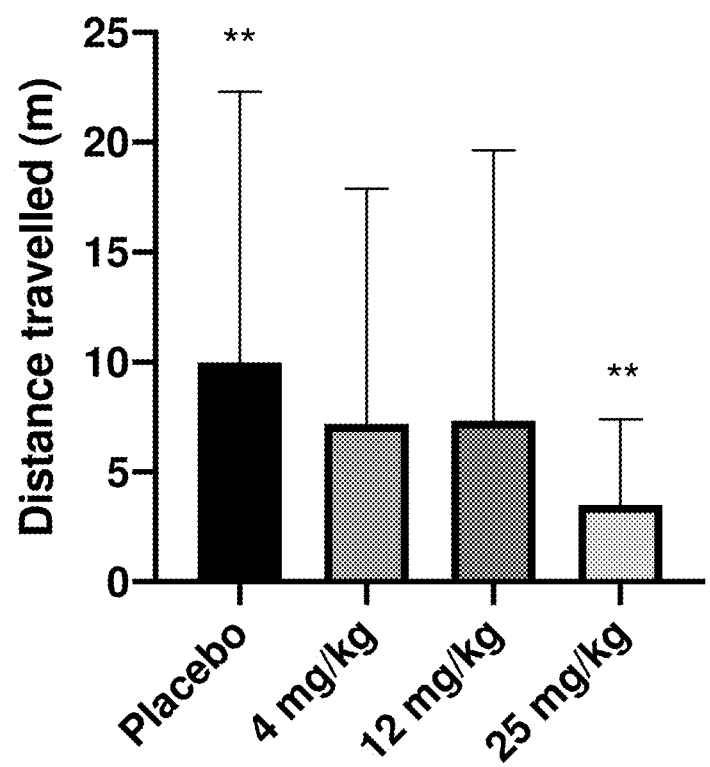
FIG. 20 is a graph showing the average distance (with standard deviation) travelled by the tested dogs across all four phases of the study during the 3-min post-thunder interval (n=16 dogs/treatment). **Distance travelled was statistically significant between placebo and 25 mg CBD/kg at p=0.05.

Using data from all four phases combined and as shown in FIG. 20

During the 3-minute post-thunder interval, the distance travelled by dogs receiving 25 mg/kg CBD (n=16 dogs) was significantly reduced by 65% as compared to dogs receiving placebo (n=16 dogs) [mean±SD=3.5±3.9 m versus 10.0±12.3 m, respectively; p=0.05];

TABLE 7

Efficacy acute anxiety canine study (n = 2 studies)

| | | | | |
|---|---|---|---|---|
| Assessment of the Anxiolytic Properties of a Cannabinoid Formulation in Beagle Dogs using a Car-Ride Model of Fear and Anxiety | R, PC, Blinded, Crossover (7-d washout between treatments) A 10-minute car ride was used to induce situational anxiety Animal behaviours were manually and video recorded | 16 adult Beagle dogs (8 M, 8 F) 3.8 to 9.6 years of age 8.8 to 13.3 kg | Animals dosed 4 hours (±10 minutes) prior to car ride via oral syringe: MCT placebo oil (n = 16 dogs) 4 mg CBD/kg (n = 16)* 12 mg CBD/kg (n = 16)* 25 mg CBD/kg (n = 16)* *CBD oils contained a CBD isolate mixed in MCT oil | Objective efficacy measures: Blood cortisol Heart rate Defecation (yes/no) Urination (yes/no) Emesis (yes/no) Lying down duration (s) Sitting duration (s) Standing duration (s) Lip licking frequency Vocalization frequency Subjective efficacy measures: Yawning score$^a$ Panting score$^a$ |

TABLE 7-continued

Efficacy acute anxiety canine study (n = 2 studies)

| Assessment of the Anxiolytic Properties of a Cannabinoid Formulation in Beagle Dogs using a Noise-Induced Model of Fear and Anxiety | R, PC, Blinded, Crossover (6-d washout between treatments) A thunderstorm noise (lasting 3 min) was used to induce situational anxiety. Animal observations were taken over a 9-min period as follows: 1 to 3 min = pre thunder (no noise) 4 to 6 min = thunder noise delivered 7 to 9 min = post thunder (no noise) Animal behaviours were audio and video recorded | 16 young Beagle dogs (8 M, 8 F) 1.3 years of age 8.1 to 15.5 kg | Animals dosed 4 hours (±10 minutes) prior to each thunderstorm test via oral syringe: MCT placebo oil (n = 16 dogs) 4 mg CBD/kg (n = 16)* 12 mg CBD/kg (n = 16)* 25 mg CBD/kg (n = 16)* *CBD oils contained a CBD isolate mixed in MCT oil | Escape attempt score[8] Salivation score[8] Other measures: Plasma CBD, 7-COOH-CBD, THC, 11-OH-THC, AEA Body weight Objective efficacy measures: Blood cortisol Heart rate Distance travelled (m) Inactivity duration (s) [sitting + lying down + standing] Subjective efficacy measures: Global Anxiety Intensity Score[b] Inactivity frequency score[c] Scanning frequency score[c] Active frequency score[8] Active intensity score[8] Other measures: Plasma CBD, 7-COOH-CBD, THC, 11-OH-THC, AEA Body weight |

Overall, the study provides a preliminary signal for a potential calming effect of CBD (12 and 25 mg/kg) to an acute stressor (thunderstorm)—treatment with CBD caused the dogs to move less both during the thunderstorm stressor (25 mg/kg) and after the stressor (12 mg/kg, 25 mg/kg).

Example 8—Anti-Anxiety Assessment of CBD in Dogs During a Chronic CBD Administration Study The present study was conducted to evaluate the potential antianxiety effects of CBD after chronic administration using a thunderstorm model of anxiety. A placebo-controlled 28-day CBD dosing, behavioral and safety study was conducted in which the anti-anxiety behavioral effects of chronic CBD were evaluated after 7 and 21 days of CBD administration. Anxiety-related behavioral assessments were conducted using a thunderstorm noise-induced model of anxiety. Four different doses of CBD isolate (1, 2, 4 and 12 mg CBD/kg dog's body weight) were administered orally, as a liquid, once a day to fasted dogs. The primary anti-anxiety measures included blood cortisol levels, heart rate, distance traveled, head movements, global anxiety and scanning behavior.

Anti-Anxiety Results:

The three lower CBD doses produced observable anti-anxiety effects as reflected by declines in a stress biomarker, body movements, visual scanning and overall global anxiety scores, as described below.

Cortisol:

The lowest 3 doses induced a decline in cortisol, a biomarker of stress, at both days 7 and 21. Chronic administration of 1 and 2 mg CBD/kg resulted in a greater decrease in cortisol on day 21 than day 7, which suggested the antianxiety effects of CBD develops over time as the blood levels of CBD become more constant. Heart rate was not affected by chronic CBD treatment.

Body Movements:

Thunderstorm-induced body movements in the dogs were generally decreased by CBD administration. Head movements were decreased by day 7 in the two lowest CBD treatment groups which suggested the overall reduction in anxiety occurred more rapidly at the 1 and 2 mg/kg doses. A decline in head movements was observed in all treatment groups on day 21.

Visual Scanning:

Analysis of the visual scanning movements indicated visual scanning was the most reduced on Day 7 by the 1 mg/kg treatment, and by the 1 and 2 mg/kg treatments on day 21, which suggested an anxiolytic response on this measure.

Global Anxiety Scores:

Global Anxiety Scores for the dogs during thunder-noise decreased after 7 and 21 days of treatment across all groups with the greatest decreases seen in the 2 mg/kg on day 7, and in the 1, 2 and 4 mg/kg groups at day 21.

Summation:

Pivotal antianxiety behavioral data generated in this preclinical study demonstrated that dogs treated with chronic CBD displayed both serum biomarker and behavioral indices of reduced anxiety.

The results of the study provide supportive evidence of the antianxiety effects of CBD in a clinical setting, in which client-owned dogs with long standing anxieties, including separation anxieties, as documented by veterinarian records, could be evaluated for therapeutic benefits derived by cannabidiol therapy.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A method for treating a long-standing anxiety or a long-standing anxiety-related disorder in a dog during or subsequently to an anxiety-inducing situation, the method comprising administering at least 1 mg/kg of cannabidiol (CBD) to the dog, wherein the administration is carried out for at least 21 days, wherein the anxiety-inducing situation is a noise.

2. The method according to claim 1, wherein the CBD is administered orally.

3. The method according to claim 2, wherein the CBD is mixed with a non-polar excipient.

4. The method according to claim 3, wherein the non-polar excipient includes a medium chain triglyceride.

5. The method according to claim 1, wherein the administration is carried out for at least 28 days.

6. The method according to claim 1, wherein the noise is a loud noise.

7. The method according to claim 6, wherein the loud noise is a storm.

8. The method according to claim 7, wherein the storm is a thunderstorm.

9. The method according to claim 1, comprising administering between about 1 mg/kg and about 12 mg/kg of CBD.

10. The method according to claim 1, comprising administering between about 1 mg/kg and about 4 mg/kg of CBD.

11. The method according to claim 1, comprising administering between about 1 mg/kg and about 2 mg/kg of CBD.

\* \* \* \* \*